United States Patent
Wu

(10) Patent No.: US 10,500,412 B2
(45) Date of Patent: Dec. 10, 2019

(54) DEVICES, SYSTEMS, AND METHODS FOR INDUCING DERMAL BLOOD VESSEL LEAKAGE

(71) Applicant: THE GENERAL HOSPITAL CORPORATION, Boston, MA (US)

(72) Inventor: Mei X. Wu, Boston, MA (US)

(73) Assignee: THE GENERAL HOSPITAL CORPORATION, Boston, MA (US)

(*) Notice: Subject to any disclaimer, the term of this patent is extended or adjusted under 35 U.S.C. 154(b) by 140 days.

(21) Appl. No.: 15/545,039

(22) PCT Filed: Jan. 22, 2016

(86) PCT No.: PCT/US2016/014451
§ 371 (c)(1),
(2) Date: Jul. 20, 2017

(87) PCT Pub. No.: WO2016/118819
PCT Pub. Date: Jul. 28, 2016

(65) Prior Publication Data
US 2018/0008838 A1 Jan. 11, 2018

Related U.S. Application Data

(60) Provisional application No. 62/106,351, filed on Jan. 22, 2015.

(51) Int. Cl.
*A61B 5/15* (2006.01)
*A61B 5/151* (2006.01)
(Continued)

(52) U.S. Cl.
CPC ............ *A61N 5/0616* (2013.01); *A61B 5/145* (2013.01); *A61B 5/14552* (2013.01);
(Continued)

(58) Field of Classification Search
CPC .... A61B 5/1405–1444; A61B 5/14503; A61B 5/1459; A61B 5/150977–150984;
(Continued)

(56) References Cited

U.S. PATENT DOCUMENTS 4,750,486 A * 6/1988 Butler .................. G02B 7/1827
606/18
5,000,752 A 3/1991 Hoskin et al.
(Continued)

OTHER PUBLICATIONS

What is Fluence? Australian Scientific Instruments. https://asi-pl.com.au/what-is-fluence/ accessed Mar. 5, 2019 (Year: 2019).*
(Continued)

*Primary Examiner* — Catherine B Kuhlman
(74) *Attorney, Agent, or Firm* — Tarolli, Sundheim, Covell & Tummino LLP

(57) ABSTRACT

The present disclosure relates generally to devices, systems, and methods for diagnosis and treatment via laser-treated skin and, more particularly, to devices, systems, and methods for inducing leakage or rupture of one or more blood vessels comprising the dermis for various diagnostic and therapeutic applications. Other aspects of the present disclosure can include methods for detecting one or more target analytes in a dermis of a subject, methods for facilitating skin-to-blood delivery of agent in a subject, and methods for collecting a fluid sample from the dermis of a subject.

9 Claims, 27 Drawing Sheets

Specification includes a Sequence Listing.

(51) Int. Cl.
*A61N 5/06* (2006.01)
*A61B 5/00* (2006.01)
*A61B 5/1455* (2006.01)
*A61B 5/145* (2006.01)
*A61M 37/00* (2006.01)
*A61N 5/10* (2006.01)
*A61N 5/067* (2006.01)

(52) U.S. Cl.
CPC .... *A61B 5/14556* (2013.01); *A61B 5/150022* (2013.01); *A61B 5/150061* (2013.01); *A61B 5/15105* (2013.01); *A61B 5/15136* (2013.01); *A61B 5/150427* (2013.01); *A61B 5/150969* (2013.01); *A61B 5/150984* (2013.01); *A61B 5/685* (2013.01); *A61M 37/0015* (2013.01); *A61B 5/150068* (2013.01); *A61B 5/150076* (2013.01); *A61M 2037/0007* (2013.01); *A61M 2037/0023* (2013.01); *A61N 5/1027* (2013.01); *A61N 2005/067* (2013.01); *A61N 2005/1021* (2013.01)

(58) Field of Classification Search
CPC .... A61B 5/15134–15136; A61B 5/157; A61B 18/20–28; A61B 2018/2005–266; A61B 2017/00765
See application file for complete search history.

(56) References Cited

U.S. PATENT DOCUMENTS

| | | | |
|---|---|---|---|
| 6,503,209 | B2 | 1/2003 | Hakky et al. |
| 9,277,964 | B1* | 3/2016 | Hasling .............. A61B 5/02042 |
| 2003/0135166 | A1* | 7/2003 | Gonnelli ........... A61M 37/0015 |
| | | | 604/264 |
| 2008/0082090 | A1* | 4/2008 | Manstein ............. A61B 18/203 |
| | | | 606/9 |
| 2008/0269735 | A1* | 10/2008 | Vila Echague ........ A61B 18/20 |
| | | | 606/15 |
| 2010/0121307 | A1* | 5/2010 | Lockard ........... A61M 37/0015 |
| | | | 604/506 |
| 2014/0163582 | A1 | 6/2014 | Austen et al. |

OTHER PUBLICATIONS

Fluence. RP Photonics Encyclopedia. https://www.rp-photonics.com/fluence.html accessed Mar. 5, 2019 (Year: 2019).*
International Search Report corresponding to International App. No. PCT/US2016/014451, dated Apr. 11, 2016, pp. 1-9.

* cited by examiner

SEQUENCE LISTING

```
<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: SYNTHETIC CONSTRUCT

<400> SEQUENCE: 1
ggggattggt tttgacgttt ttgcg                                         25

<210> SEQ ID NO 2
<211> LENGTH: 30
<212> TYPE: DNA
<213> ORGANISM: Artificial Sequence
<220> FEATURE:
<223> OTHER INFORMATION: SYNTHETIC CONSTRUCT

<400> SEQUENCE: 2
aagcattaaa taaagcgaat acatccttat                                    30

<210> SEQ ID NO 3
<211> LENGTH: 22
<212> TYPE: DNA
<213> ORGANISM: Artificial Sequence
<220> FEATURE:
<223> OTHER INFORMATION: SYNTHETIC CONSTRUCT

<400> SEQUENCE: 3
ctgggacgac atggagaaga tc                                            22

<210> SEQ ID NO 4
<211> LENGTH: 24
<212> TYPE: DNA
<213> ORGANISM: Artificial Sequence
<220> FEATURE:
<223> OTHER INFORMATION: SYNTHETIC CONSTRUCT

<400> SEQUENCE: 4
gtctcaaaca tgatctgggt catc                                          24

<210> SEQ ID NO 5
<211> LENGTH: 9
<212> TYPE: PRT
<213> ORGANISM: Plasmodium yoelii

<400> SEQUENCE: 5
```

-continued

```
Ser Tyr Val Pro Ser Ala Glu Gln Ile
1               5

<210> SEQ ID NO 6
<211> LENGTH: 9
<212> TYPE: PRT
<213> ORGANISM: Plasmodium yoelii

<400> SEQUENCE: 6

Ser Tyr Val Pro Ser Ala Glu Gln Ile
1               5
```

DEVICES, SYSTEMS, AND METHODS FOR INDUCING DERMAL BLOOD VESSEL LEAKAGE

RELATED APPLICATION

This application claims the benefit of U.S. Provisional Patent Application Ser. No. 62/106,351, filed Jan. 22, 2015, the entirety of which is hereby incorporated by reference for all purposes.

TECHNICAL FIELD

The present disclosure relates generally to devices, systems, and methods for diagnosis and treatment via laser-treated skin and, more particularly, to devices, systems, and methods for inducing leakage or rupture of one or more blood vessels comprising the dermis for various diagnostic and therapeutic applications.

BACKGROUND

The ability to quantify circulating biomarkers in a timely fashion is crucial for monitoring diseases, organ functions, and drug abuse, so there have been considerable efforts towards developing more convenient and reliable technologies for measuring blood biomarkers. Among the technologies, finger-prick has revolutionized our way to monitor plasma glucose levels in patients with diabetics. However, the technology is highly dependent on readable signals, suitable only for relatively abundant analytes in the serum so far. Most of current methods for measuring circulation biomarkers still rely on blood collection that requires a high level of medical training, as well as time-consuming, labor-intensive blood sample process, storage, and analysis. There are great challenges to develop alternative, rapid, sensitive, and reliable technologies for point-of-care molecular diagnosis.

Recently, microneedle (MN) array-based minimally invasive diagnosis has attracted attention for rapidly detecting blood biomarkers through the skin. Several surface-modified MN arrays have been fabricated, capable of recognizing circulating viral proteins and specific antibodies in mouse dermis, allowing biomarker detection without blood collection and sample processing. Unfortunately, such arrays have two key drawbacks. Concentrations of most blood biomarkers in the upper dermis are too low to be captured by MN arrays. Hence, deep dermal penetration and prolonged application are required to surmount this flaw, which is likely to cause pain, compromising patient compliance. Secondly, there are unacceptably large variations in probe bindings to individual MNs within the same array, due to uncharacterized leakage of biomarkers through capillaries damaged by penetrating MNs. After all, only a few MNs in each array cause such unintended damage and display strong binding, whereas most of the MNs in the array show no or weak capture of plasma biomarkers. Such high variability makes it impossible to quantify multiple biomarkers in one array, or reliably measure a single biomarker for quantity-based diagnosis and/or prognosis.

SUMMARY

In one aspect, the present disclosure can include a device comprising at least one penetration member that is coupled to a laser source. The least one penetration member can have a body defined by oppositely disposed proximal and distal ends. The body can have a length such that at least a portion of the distal end extends into a dermis of the skin of a subject when the device is contacted with the subject's skin. The laser source can be coupled to the at least one penetration member so that, upon activation, the laser source delivers a laser beam into the dermis for a time sufficient to induce leakage or rupture of at least one blood vessel comprising the dermis.

Another aspect of the present disclosure can include a method for inducing leakage or rupture of a blood vessel comprising the dermis of a subject. One step of the method can include contacting a device with the skin of a subject so that at least a distal end of one or more penetrating members comprising the device directly contacts the dermis. A laser source coupled to the device can be activated to deliver a laser beam to the dermis for a time sufficient to induce leakage or rupture of at least one blood vessel comprising the dermis.

Another aspect of the present disclosure can include a method for detecting a target analyte in a dermis of a subject. One step of the method can include contacting a device with the skin of a subject so that at least a distal end of one or more penetrating members comprising the device directly contacts the dermis. At least a portion of the distal end that contacts the dermis can be coated with one or more detection reagents. A laser source coupled to the device can be activated for a time sufficient to induce leakage or rupture of at least one blood vessel comprising the dermis. The target analyte, if present, can be detected in a fluid leaked from the blood vessel.

Another aspect of the present disclosure can include a method for facilitating skin-to-blood delivery of an agent in a subject. One step of the method can include contacting a device with a target skin area of a subject so that at least a distal end of one or more penetrating members comprising the device directly contacts the dermis. A laser source coupled to the device can be activated to deliver a laser beam to the dermis for a time sufficient to induce leakage or rupture of at least one blood vessel comprising the dermis. The agent can be administered to the target skin area.

Another aspect of the present disclosure can include a method for collecting a fluid sample from the dermis of a subject. One step of the method can include contacting a device with the skin of a subject so that at least a distal end of one or more penetrating members comprising the device directly contacts the dermis. A laser source coupled to the device can be activated to deliver a laser beam to the dermis for a time sufficient to induce leakage or rupture of at least one blood vessel comprising the dermis. A volume of a fluid leaked from the at least one blood vessel can be collected.

Another aspect of the present disclosure can include a method for inducing leakage or rupture of a blood vessel comprising the dermis of a subject. One step of the method can include activating a laser source to apply a laser beam to a target skin area of the subject for a time sufficient induce leakage or rupture of at least one blood vessel comprising the dermis. A device can be contacted with the at least one target skin area so that at least a distal end of one or more penetrating members comprising the device directly contacts the dermis (e.g., after laser illumination).

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 8A shows fluorescence images of anti-FITC-microneedles (MNs) and C-MNs. The MNs were incubated with 2.5 mM FITC in 2% BSA solution at 36° C. for 2 h and photographed by fluorescent microscopy. FITC intensity consistently displays binding to anti-FITC-MNs but not C-MNs when concentration (FIG. 8B) or incubation time (FIG. 8C) is varied (n=6). FIG. 8D shows detection of circulating FITC in vivo. FITC was i.v. administered into mice, after which C-MNs (unfilled circle) and anti-FITC-MNs (filled square) were applied into the dorsal skin of the mice. The patches were removed at indicated times and fluorescence intensity in each array was determined. Each symbol represents one array containing 9 MNs, and a dashed horizontal line is a cutoff value for positive FITC binding on the array, which is defined as the mean value of c-MNs plus 3×standard deviation. Insets in FIG. 8D show fluorescence images of one C-MN array (left) and one anti-FITC array (right) (scale=100 mm);

FIG. 9A shows that FITC extravasation occurs rapidly in the skin illuminated by 532 nm NYL laser with a fluence of 0.5 J/cm$^2$. Intravital laser confocal microscopy was used to track FITC signal over time after laser illumination in the skin of mice that had received FITC intravenously. Control skin was shown after illumination with sham light in the same mice. FIG. 9B shows diffusion of Evans blue dye throughout the dermis after laser illumination. FIG. 9C shows Evans blue intensity increases in upper dermis by more than 1000 times in laser treated skin as compared with non-laser-treated skin. FIG. 9D shows histological analysis of control and laser-treated skin. Arrows indicate a capillary vessel (scale=200 mm in FIG. 9A, 50 mm in FIG. 9B, 100 mm in FIG. 9D (upper) or 5 mm in FIG. 9D (bottom));

FIG. 10A shows that CMNs (unfilled circle) and anti-FITC-MNs (filled square) were applied into laser-treated skin for indicated times in mice receiving FITC intravenously. Each symbol represents one array consisting of 9 MNs. The cutoff value is indicated by a dashed line and defined as FIG. 8D. Inset shows fluorescence images of one anti-FITC-MN array. Note, all MNs in the array show uniform and strong FITC binding (scale=100 mm). FIG. 10B shows that the amounts of circulating FITC measured by anti-FITC-MNs are similar to those obtained with fluorescence spectrophotometer. Anti-FITC-MNs or C-MNs were inserted into laser-treated skin for 30 min in mice receiving varying amounts of FITC intravenously, and the FITC captured on MNs was calculated by FITC intensity in comparison with a standard curve run in parallel;

FIG. 11A shows fluorescence intensity analysis demonstrates specific binding of anti-HA IgG to HA-MNs, but not to OVA-MNs in serum from immunized mice or naive mice. FIG. 11B shows a standard curve of FITC intensity on HA-MNs vs. known concentrations of anti-HA IgG. FIG. 11C shows a specific and sensitive capture of circulating anti-HA IgG in immunized mice. HA-MNs of 30 mm or 100 mm in length were inserted into laser-treated skin for 30 min. The MNs were removed and incubated with FITC-conjugated secondary antibody. FITC intensity was measured as FIG. 11A. OVA-MNs of 100 mm in length were inserted into laser-treated skin by a procedure similar as negative controls. A dashed horizontal line is a cutoff value for positive FITC binding on the array as defined in FIG. 8D. FIG. 11D shows a comparison of the concentrations of circulating anti-HA IgG measured by HA-MNs at different lengths in the presence or absence of laser treatment, as well as by a conventional IF assay of the corresponding serum (serum) (n=6);

FIG. 12A is a series of photos showing Evans blue dye leakage in laser-irradiated skin as compared to non-laser treated skin. FIGS. 12B-C show increases in Evans blue fluorescence in laser-irradiated dermis (FIG. 12B) and in fluorescence intensity in the upper dermis in comparison with non-irradiated counterpart (FIG. 12C). FIG. 12D shows that skin reactions at indicated times after subject to 595 nm laser at 4 J/cm$^2$ (scale=5 mm in FIG. 12A and FIG. 12D or 100 mm in FIG. 12B);

FIG. 13A shows that the amount of anti-HA IgG captured in the upper dermis was comparable to that in deep dermis after laser illumination. A dashed horizontal line is a cutoff value for positive FITC binding on the array as defined in FIG. 8D. FIG. 13B shows that the amount of anti-HA IgG in the upper dermis or dermis detected by MNs was similar to that in serum samples measured by conventional IF assays (serum);

FIG. 14A shows the skin without laser treatment. FIG. 14B shows strong capture of circulating biomarkers occurs only on an MN that is physically close to a damaged capillary vessel like MN #1, but not on an MN that is away from an injured vessel like MN #3 in the absence of laser treatment. In contrast, all MNs on the array are exposed to uniformly high concentrations of circulating biomarkers in laser-treated skin owing to laser-induced extravasation (FIG. 14C);

FIG. 15A shows representative images showing blood vessel leakage induced by laser. Blood vessels were marked by IV injected FITC dextran, after which the dorsal skin of the mice was treated by different lasers and examined under an intravital confocal microscope within 30 min. FIG. 15B shows representative histological examination of laser-treated skins. FIG. 15C shows alterations of blood vessels induced by lasers. Bar=100 μm in FIGS. 15A-B or 10 μm in FIG. 15C. Arrows indicate blood vessels (n=5);

FIG. 16A is a standard curve of liver parasite loads after IV injection of indicated numbers of sporozoites. FIG. 16B shows the effects of laser skin illumination on skin-to-liver delivery of sporozoites. Mice were injected with 4,000 sporozoites either by an IV route or through ID injection into laser-treated or un-treated dorsal skin (ID). The liver parasite loads were determined by RT-qPCR and estimated using the standard curve in FIG. 16A. In FIGS. 16C-D, GFP+ cells were measured by flow cytometry 42 h after freshly isolated PyGFP sporozoites were injected by IV or ID in the presence or absence of laser treatment (FIG. 16C). Liver parasite loads were quantified by RT-qPCR in the animals (FIG. 16D). Results are expressed as means±standard deviation (SD). The experiment was repeated twice with similar results (n=8, $*p<0.05$, $p<0.01$, $*p<0.001$, and ns, not significant);

In FIG. 17A, blood vessels were marked by Texas red-dextran (MW 70,000). FIGS. 17B-C are representative images of CFSE-stained sporozoites in untreated (FIG. 17B) or laser-treated skin (FIG. 17C). Bar=10 μm. FIG. 17D shows percentages of sporozoites in association with vessel walls or inside the vessels. Data are shown as means±SD (n=10, $***p<0.001$);

DETAILED DESCRIPTION

Definitions

Figure 1A:
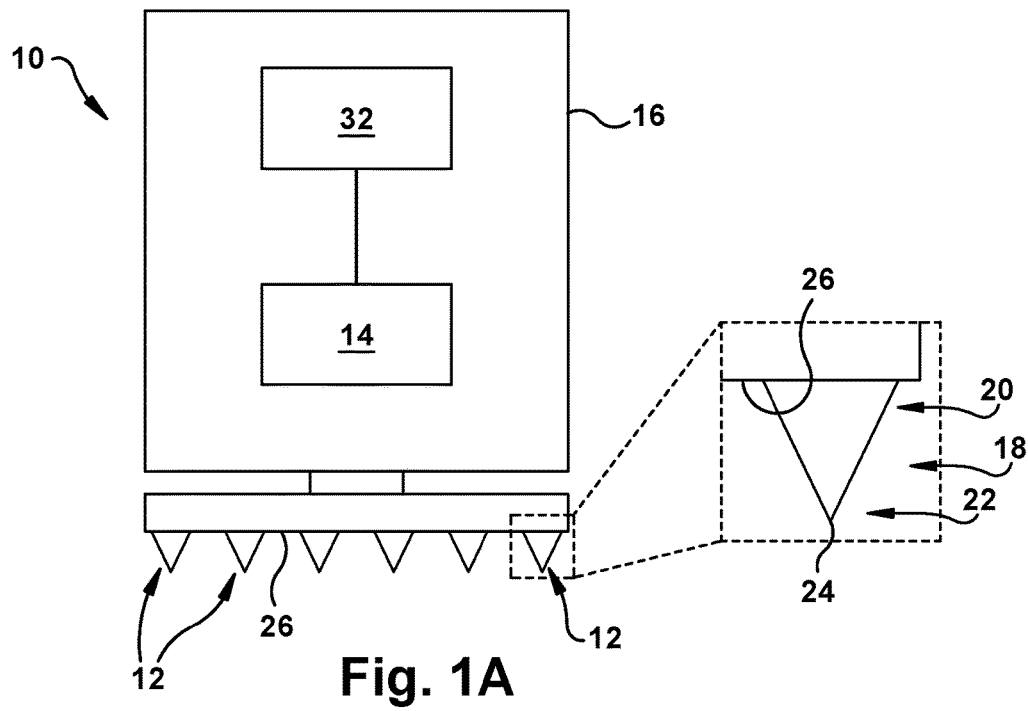
FIG. 1A is a schematic illustration showing a device for inducing leakage of a dermal blood vessel constructed in accordance with one aspect of the present disclosure.

Unless defined otherwise, all technical and scientific terms used herein have the same meaning as is commonly understood by one of skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items or elements.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature may not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure.

The sequence of operations (or acts/steps) is not limited to the order presented in the claims or figures unless specifically indicated otherwise.

As used herein, the terms "about" or "approximately" can generally mean within 20 percent, within 19 percent, within 18 percent, within 17 percent, within 16 percent, within 15 percent, within 14 percent, within 13 percent, within 12 percent, within 11 percent, within 10 percent, within 9 percent, within 8 percent, within 7 percent, within 6 percent, within 5 percent, within 4 percent, within 3 percent, within 2 percent, or within 1 percent of a given value or range. Numerical quantities given herein are approximate, meaning that the term "about" or "approximately" can be inferred if not expressly stated.

As used herein, the term "target analyte" can refer to a substance in a fluid sample capable of being detected and analyzed by the present disclosure. Target analytes can include, but are not limited to, molecules, peptides, proteins (including prions), nucleic acids, oligonucleotides, cells (e.g., cancer cells), microorganisms and fragments and products thereof (e.g., viruses, bacteria, fungi, fungi), enzyme substrates, ligands, carbohydrates, hormones, sugar, metabolic byproducts, cofactors, pollutants, chemical agents, small molecules, drugs (e.g., illicit drugs), toxins, plants and fragments and products thereof, biomarkers indicative of a disease or disorder, and any substance for which attachment sites, binding members or receptors can be developed.

As used herein, the term "fluid sample" can refer to any quantity of a liquid or fluid that may comprise one or more target analytes and that can be used (e.g., assayed) with the present disclosure.

As used herein, the term "operatively coupled" can mean permanently or temporarily in physical or electrical communication so that a component functions in a complementary or consistent manner with another component. "Physical communication" can refer to physical connection (e.g., direct physical connection) between components (e.g., via a wire).

As used herein, the term "electrical communication" can refer to the ability of a generated electric field to be transferred to, or have an effect on, one or more components of the present disclosure. In some instances, the generated electric field can be directly transferred to a component (e.g., via a wire or lead). In other instances, the generated electric field can be wirelessly transferred to a component.

As used herein, the term "detection reagent" can refer to any agent that is capable of binding to, capturing, or reacting with, a target analyte. In some instances, a "detection reagent" can include an agent that is capable of specifically binding to a target analyte, i.e., having a higher binding affinity and/or specificity to the target analyte than to any other moiety. Any agent can be used as a detection reagent so long that it has the desired binding affinity and/or specificity to the target analyte. Examples of detection reagents can include, but are not limited to, antibodies, antibody fragments, recombinant antibodies and fragments thereof, aptamers, native, synthetic, or recombinant peptides or proteins, peptoids, cell receptors and fragments thereof, enzymes, enzymes involved in the production of reactive oxygen species or breakdown, enzymes that catalyze a reaction leading to a product that may be of research, diagnostic or therapeutic use, p450 enzymes, glycoproteins, oligonucleotides, nucleic acids (e.g., RNA, DNA, RNA/DNA hybrids), peptide-nucleic acids, vitamins, sugars, oligosaccharides, carbohydrates, lipids, lipoproteins, small molecules, chemical compounds (e.g., hydrogen peroxide), cells, a cellular organelle, an inorganic molecule, an organic molecule, and mixtures or complexes thereof. It will be appreciated that detection reagents may also be coupled to certain substrates, such as microbeads.

As used herein, the term "point-of-care environment" can refer to real-time performance of the methods disclosed herein (e.g., diagnostic testing) that can be done in a rapid time frame (e.g., so that the resulting test is performed faster than comparable tests that do not employ the present disclosure). Point-of-care environments can include, but are not limited to: emergency rooms; at a bedside; in a stat laboratory; operating rooms; hospital laboratories and other clinical laboratories; doctor's offices; or in any situation or locale where a rapid and accurate result is desired.

As used herein, the term "onsite" can refer to any situation or locale, other than a point-of-care environment, where real-time performance of the methods disclosed herein is desired and can be done in a rapid time frame. Non-limiting examples of onsite situations or locales can include on the side of a road or highway, in a police station, and in a work place.

As used herein, the term "agent" can refer to any compound, molecule, or substance that is capable of being administered (e.g., injected) into a subject, either in a pure (or substantially pure form) or admixed with a suitable carrier or excipient. Non-limiting examples of agents can include therapeutic agents (e.g., pharmaceutical compounds) and imaging agents.

As used herein, the term "therapeutic agent" can refer to any compound, molecule, or substance useful for therapeutic or diagnostic purposes (e.g., for the treatment of a disease or condition). Therapeutic agents can include, without limitation, drug-like molecules, chemotherapeutic agents, radioactive material, proteins, peptides, antibodies, antibody fragments, aptamers and small molecules. Protein therapeutic agents can include, without limitation, peptides, enzymes, structural proteins, receptors, and other cellular or circulating proteins as well as fragments and derivatives thereof. In one example, a therapeutic agent can include a vaccine, such as radiation-attenuated malaria sporozoites.

As used herein, the term "imaging agent" can refer to substances or molecules that can be used to image tissues or cells, such as those of a living organism, for purposes of diagnosis, therapy, image-guided surgery, and the like. Imaging agents typically contain a dye that is capable of absorption of electromagnetic radiation, typically in the ultraviolet (UV), visible, or near infrared (NIR) range. Imaging agents can also be capable fluorescent emission, such as in the visible or NIR range. An optical signal detected from the dye or conjugate can be, for example, absorption or fluorescent emission. Those skilled in the art can readily identify imaging agents for use with the present disclosure.

As used herein, the term "labeling agent" can refer to a compound or other agent used to label a molecule or molecules of interest, such as a detection reagent, thereby providing a detectable signal for subsequent detection. Examples of labeling agents can include biotin, streptavidin, fluorophores, quantum dots, and the like. Those skilled in the art will appreciate other types of labeling agents.

As used herein, the term "skin" can refer to the soft outer covering of vertebrates. The skin can interface with the environment and act as the first line of defense from external factors. For example, the skin can include the epidermis (e.g., including the outermost layers of cells in the skin) and the dermis (e.g., a layer of skin between the epidermis and subcutaneous tissue that cushions the body from stress and strain).

As used herein, the term "dermis" can refer to the fibrous inner layer of the skin just beneath the epidermis. The dermis is derived from the embryonic mesoderm, varies from about 0.05 cm to 0.3 cm in thickness, is well supplied with nerves and blood vessels, and contains hair roots, sebaceous glands, and sweat glands. The dermis is formed of two layers: an upper dermal layer (stratum papillare), which forms an upward projection between the epidermal rete pegs; and a deeper dermal layer (stratum reticulare) that contains and supports dermal nerves, blood vessels and lymphatics, and also overlies subcuticular fat layer and superficial fascia.

As used herein, the term "upper dermis" can refer to the papillary region or stratum papillare of the dermis, which is made of loose connective tissue.

As used herein, the term "laser source" can refer generally to a category of optical devices that emit a spatially and temporally coherent beam of light otherwise known as a laser beam. In some instances, the term can refer to one or more light emitting devices that emits light through the stimulated emission of electromagnetic radiation In one example, the term "laser source" can refer to conventional lasers (e.g., CO2, YAG, and fiber lasers), as well as laser diodes and LED.

As used herein, the term "laser beam" can refer to light emitted by a laser source. In some instances, a laser beam, generated by a laser source, can be continuous or pulsatile and have a wavelength, pulse width, and fluence/energy as provided below. For example, a laser beam can have a wavelength of about 1,000 nm to about 400 nm, e.g., about 1,000 nm to about 900 nm, about 900 nm to about 800 nm, about 800 nm to about 700 nm, about 700 nm to about 600 nm, about 600 nm to about 500 nm, or about 500 nm to about 400 nm. In another example, a laser beam can have a wavelength that excites at least one of hemoglobin and oxyhemoglobin, e.g., about 540 nm and 578 nm, respectively. In some instances, a laser beam can have a pulse width of about 10 ns to about 2 ns, for example, about 9 ns, about 8 ns, about 7 ns, about 6 ns, about 5 ns, about 4 ns, or about 3 ns. In other instances, a laser beam can have a pulse width of about 0.01 ms to about 0.1 ms, about 0.1 ms to about 0.2 ms, about 0.2 ms to about 0.3 ms, about 0.3 ms to about 0.4 ms, about 0.4 ms to about 0.5 ms (e.g., at or about 0.45 ms), about 0.5 ms to about 0.6 ms, about 0.6 ms to about 0.7 ms, about 0.7 ms to about 0.8 ms, about 0.8 ms to about 0.8 ms, about 0.8 ms to about 0.9 ms, or about 0.9 ms to about 1.0 ms or greater. In another example, a laser beam can have a fluence/energy of about 1 $W/cm^2$ to about 0.001 $W/cm^2$, e.g., about 0.9 $W/cm^2$, 0.8 $W/cm^2$, 0.7 $W/cm^2$, 0.6 $W/cm^2$, 0.5 $W/cm^2$, 0.4 $W/cm^2$, 0.3 $W/cm^2$, 0.2 $W/cm^2$, 0.1 $W/cm^2$, 0.09 $W/cm^2$, 0.08 $W/cm^2$, 0.07 $W/cm^2$, 0.06 $W/cm^2$, 0.05 $W/cm^2$, 0.04 $W/cm^2$, 0.03 $W/cm^2$, 0.02 $W/cm^2$, 0.01 $W/cm^2$, 0.009 $W/cm^2$, 0.008 $W/cm^2$, 0.007 $W/cm^2$, 0.006 $W/cm^2$, 0.005 $W/cm^2$, 0.004 $W/cm^2$, 0.003 $W/cm^2$, or 0.002 $W/cm^2$.

In another example, the laser beam can have a fluence of about 5-35 $J/cm^2$, e.g., about 7.5-8.5 $J/cm^2$, about 8.5-9.5 $J/cm^2$, about 9.5-10.5 $J/cm^2$, about 10.5-11.5 $J/cm^2$, about 11.5-12.5 $J/cm^2$, about 12.5-13.5 $J/cm^2$, about 13.5-14.5 $J/cm^2$, about 14.5-15.5 $J/cm^2$, about 15.5-16.5 $J/cm^2$, about 16.5-17.5 $J/cm^2$, about 17.5-18.5 $J/cm^2$, about 18.5-19.5 $J/cm^2$, or about 19.5-20 $J/cm^2$ to induce or cause rupture of one or more blood vessels comprising the dermis.

In yet another example, the laser beam can have a fluence of less than about 4 $J/cm^2$ (e.g., less than 4 $J/cm^2$), e.g., about 3.5-4 $J/cm^2$, about 3-3.5 $J/cm^2$, about 2.5-3 $J/cm^2$, about 2-2.5 $J/cm^2$, about 1.5-2 $J/cm^2$, about 1-1.5 $J/cm^2$, about 1 $J/cm^2$, or less than about 1 $J/cm^2$ to induce leakage, but not rupture, of one or more blood vessels comprising the dermis.

As used herein, the term "Class I laser" can refer to a laser that is incapable of producing damaging radiation levels.

As used herein, the term "Class II laser" can refer to a laser that emits radiation in the visible portion of the spectrum. Such a laser may be hazardous if viewed directly for extended periods of time.

As used herein, the term "Class III laser" can refer to either a Class IIIa or Class IIIb laser. Class IIIa lasers are those that normally would not produce injury if viewed only momentarily with the unaided eye. They may present a hazard if viewed using collecting optics, e.g., telescopes, microscopes, or binoculars (e.g., HeNe lasers above 1 milliwatt but not exceeding 5 milliwatts radiant power). Class IIIb lasers can cause severe eye injuries if beams are viewed directly or specular reflections are viewed (e.g., visible HeNe lasers above 5 milliwatts but not exceeding 500 milliwatts radiant power).

As used herein, the terms "leakage" or "leaky", when referring to a blood vessel comprising at least a portion of the dermis that has been exposed to a laser beam of the present disclosure, can refer to efflux of certain, but not all, blood vessel constituents from the blood vessel. For example, a leaky blood vessel may have a number of perforations sufficient to permit efflux of one or more target analytes therefrom into surrounding tissue (e.g., dermal tissue), but not certain cell types, such as red blood cells (RBCs).

As used herein, the term "rupture", when referring a blood vessel comprising at least a portion of the dermis that has been exposed to a laser beam of the present disclosure, can refer to breakage or bursting of the blood vessel so that normal blood flow through the blood vessel is not possible and spillage of blood constituents into the surrounding tissue (e.g., dermis) results.

As used herein, the term "leaked fluid" can refer to a fluid that is leaked from a blood vessel comprising the dermis after exposure to a laser beam of the present disclosure. In some instances, the leaked fluid may not contain any cells typically present in the blood vessel, such as RBCs, and/or one or more target analytes. In other instances, the leaked fluid may contain cells (e.g., RBCs, cancer cells, etc.).

As used herein, the term "microneedle" can refer to an elongated, hollow structure typically having a sharpened tip. In some instances, a microneedle can be sufficiently long to penetrate through the stratum corneum skin layer and the epidermal layer into the dermis, yet sufficiently short so as to not penetrate to the subcutaneous fat layer. Non-limiting examples of microneedles that may be used in the present disclosure include those disclosed in U.S. Pat. Nos. 6,652,478 and 6,908,453.

As used herein, the term "microprojection" can refer to elements adapted to penetrate or pierce the stratum corneum or other biological membranes. In some instances, a microneedle can be a microprojection. Non-limiting examples of microprojections that may be used in the present disclosure can include those disclosed in U.S. Pat. No. 8,219,574.

As used herein, the term "array" can refer to an orderly arrangement of penetration members (e.g., microneedles or microprojections). This may include a rectangular, circular, oval, polygonal, or similarly shaped arrangement of quantities in rows and columns, as in a matrix. The totaling penetration members of the array can be 2 or more, e.g., an array may be 1×2, 1×3, 2×2, 2×3, 10×10, 50×50, 100×100, 200×200, and so on.

As used herein, the terms "computer-readable medium" or "computer-readable instructions" can refer to any tangible storage and/or transmission medium that participate in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

As used herein, the term "pharmaceutical compound" can refer to any drug used for the diagnosis, cure, treatment, or prevention of disease. The terms "pharmaceutical compound" and "drug" can be used interchangeably herein.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

Overview

The present disclosure relates generally to devices, systems, and methods for diagnosis and treatment via laser-treated skin and, more particularly, to devices, systems, and methods for inducing leakage or rupture of one or more blood vessels comprising the dermis for various diagnostic and therapeutic applications. Lasers have been used in dermatology for more than 20 years. Such lasers, which are directed to the skin surface, require a high light energy can be blunted by the skin pigment melanin. Melanin absorbs light mainly at a spectral region between 335-700 nm, overlapping with that of hemoglobin and oxyhemoglobin (532-597 nm). Melanin is produced by melanocytes located in the basal layer of the epidermis, which then diffuse into the epidermis and are present at a high concentration in dark skin. The content of melanin in the skin adversely affects the efficacy of laser-induced vascular permeability.

By directly illuminating the dermis (as opposed to the skin surface), the devices and methods of the present disclosure avert the interference of melanin and thereby induce leakage of the dermis (e.g., the upper dermis) in a safe and efficient manner. There are several advantages gained by direct illumination of the dermis as opposed to the skin surface, such as: (1) inducing vascular (dermal) permeability irrespective of skin color and thickness of the epidermis; (2) substantially lowering the laser energy required to induce vascular permeability; and (3) providing an extremely safe and effective technique for inducing vascular permeability (e.g., by eliminating laser exposure to patients and medical staff and obviating the requirement for protection (e.g., goggles) during application). Based at least on these advantages, and as discussed in more detail below, the present disclosure provides devices, systems, and methods for inducing leakage or rupture of one or more blood vessels comprising the dermis for various diagnostic and therapeutic applications, such as methods for detecting one or more target analytes in a dermis of a subject, methods for facilitating skin-to-blood delivery of agent in a subject, and methods for collecting a fluid sample from the dermis of a subject.

Devices and Systems

One aspect of the present disclosure can include devices and systems for inducing leakage or rupture of a blood vessel comprising the dermis of a subject. In some instances, a device 10 (FIG. 1A) for inducing leakage or rupture of a blood vessel comprising the dermis of a subject can comprise at least one penetration member 12 that is coupled (e.g., operatively coupled) to a laser source 14. As discussed in more detail below, the laser source 14 can be coupled to the at least one penetration member 12 so that, upon activation, the laser source delivers a laser beam into the dermis for a time sufficient to induce leakage or rupture of at least one blood vessel comprising the dermis. In some instances, devices 10 of the present disclosure can be configured as a hand-held unit to permit convenient point-of-care or onsite operation. As such, all or some of the components comprising the devices 10 and systems described herein may be included in a single, portable unit.

Referring to FIG. 1A, a device 10 of the present disclosure can include a housing 16 within or to which certain components (described below) are connected or coupled. In some instances, the housing 16 can be ergonomically sized and dimensioned to fit within the hand of a user (e.g., medical personnel, such as a physician). The housing 16 can be made of any suitable material(s), such as hardened plastics, metals, etc.

The at least one penetration member 12 comprising the device 10 can include a body 18 defined by oppositely disposed proximal and distal ends 20 and 22. The body 18 can have a length such that at least a portion of the distal end 22 (e.g., a distal tip 24) extends into a dermis (e.g., upper dermis) of the skin of subject when at least a portion of the device 10 is contacted with the subject's skin. In some instances, the at least one penetration member 12 can be connected (e.g., directly connected) to the housing 18. The at least one penetration member 12 can comprise a needle, a microneedle, or a microproject. Where more than one penetration member 12 is included as part of the device 10, the penetration members can be arranged, or comprise, an array. Although the illustrative devices 10 described herein all include multiple penetration members 12, it will be understood that devices and systems of the present disclosure may include only one penetration member.

Figure 1B:
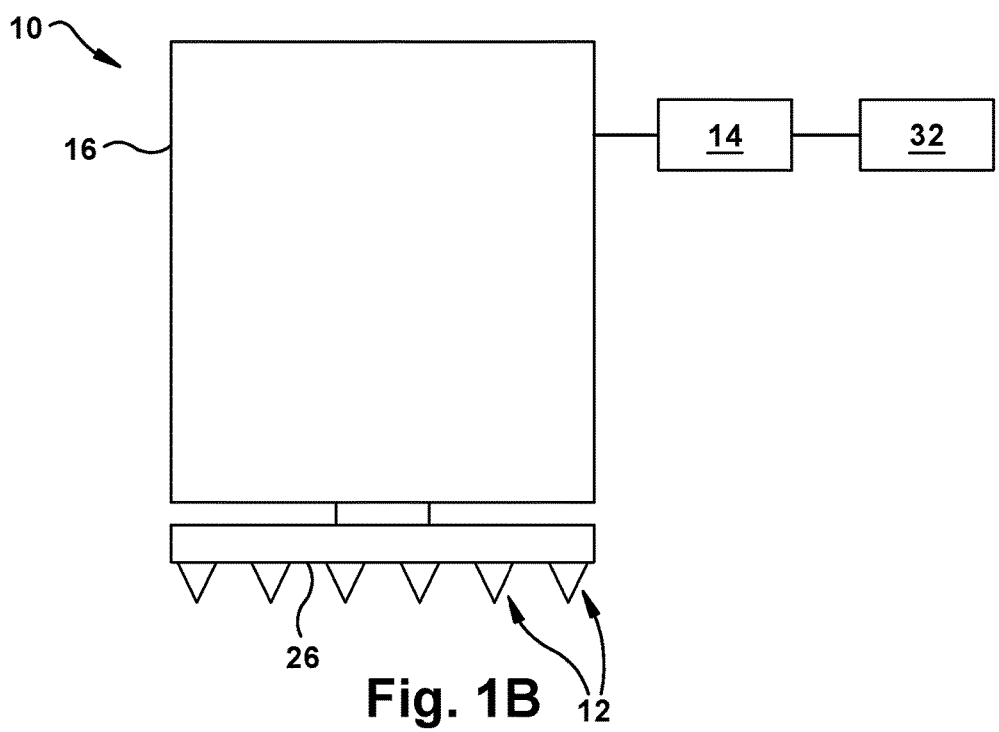
FIG. 1B is a schematic illustration showing an alternative configuration of the device in FIG. 1A.

As shown in FIGS. 1A-B, a device 10 is illustrated with multiple penetration members 12 (e.g., microneedles) protruding from a surface 26 of the housing 18. The penetration members 12 may be arranged in any desired pattern or distributed over the surface 26 uniformly or randomly. Some or all of the penetration members 12 can be transparent or non-transparent. In some instances, some or all of the penetration members 12 may be solid and made of a transparent material such that a laser beam, when directed to the penetration member(s), are conveyed through the penetration member(s) directly into the dermis. In one example, solid penetration members 12 can be created as described by Li et al., Biomaterials, 59:30-38 (2015) (e.g., using PMMA). Alternatively, solid penetration members 12 (e.g., microneedles) can be created as described by Li et al., 2015, except that graphene (GR) is used to make the microneedles. For example, a mixture of PMMA powder with a solution of monomer (azobisisobutyronitrile, CDH) in which GR is dispersed can be poured into a PDMS mold of microneedles (the concentration of GR can be about 0.1-2%). After being heated at about 90° C. for about 48 hours, the formed transparent microneedles can be peeled off from the molds and used to form a device 10 of the present disclosure.

Figure 2A:
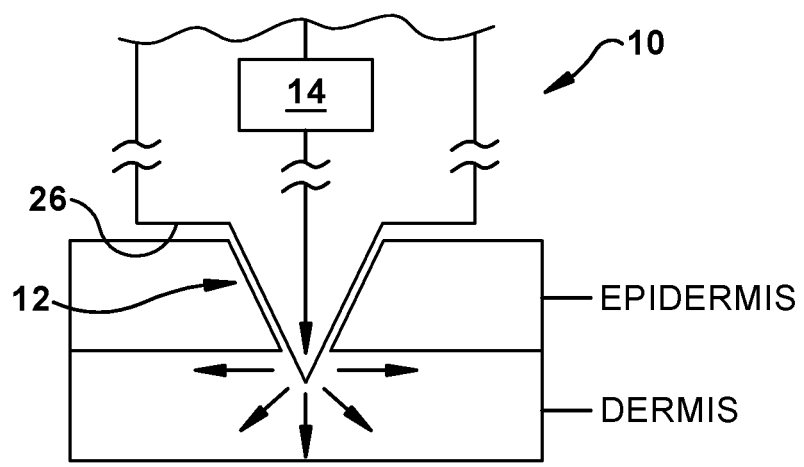
FIG. 2A is a magnified schematic illustration showing direct application of a laser beam to the dermis via a device of the present disclosure.
Figure 2B:
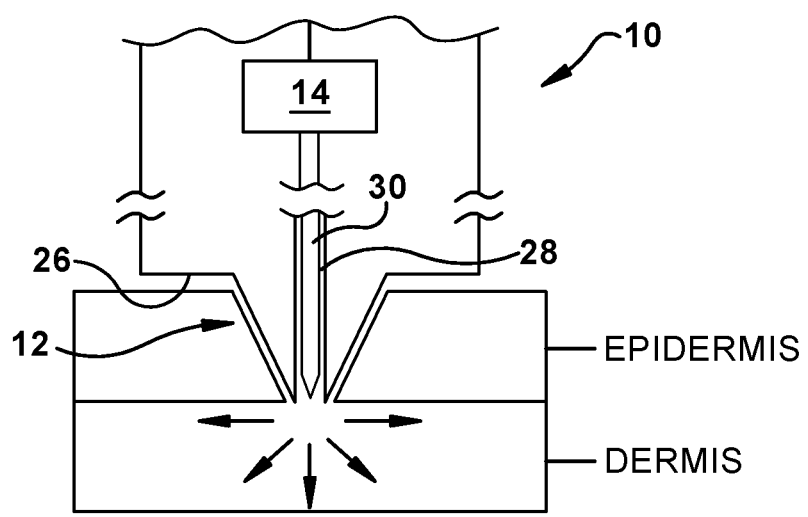
FIG. 2B is a magnified schematic illustration showing direct application of a laser beam to the dermis via another device of the present disclosure.

In other instances, some or all of the penetration members 12 can include a channel 28 (FIG. 2B) that extends between the proximal and distal ends 20 and 22 of each penetration member. The channel 28 can be sized and dimensioned to receive one or more optical fibers 30 (e.g., that is/are operatively coupled to the laser source 14). In such instances, a laser beam generated by the laser source 14 can be transmitted via the optical fiber 30 to directly illuminate the dermis upon bypassing the epidermis and the basal layer of the epidermis. The laser beam can irradiate the dermis, raising the permeability of all blood vessels (e.g., capillaries) surrounding each penetration member 12. Advantageously, any interference of melanin can be effectively circumvented by directly illuminating of the dermis. By "directly illuminating the dermis", it is meant that the first tissue contacted by the laser beam is the dermis; in other words, the laser beam does not illuminate any other skin layer (e.g., the epidermis) before reaching the dermis.

The general shape of the penetration members 12 can be tapered (e.g., conical). For example, each of the penetration members 12 can have a larger base at the surface 26 and extend away from the surface, tapering towards a distal tip 24. Although many penetration members 12 may have a uniform slope or wall angle (with respect to, e.g., a z-axis normal to the surface), penetration members may have different wall angles. For example, penetration members 12 can include an upper section having steeper wall angles with respect to the surface 26, and a lower section proximate the distal tip 24 having shallower wall angles. In further shape variations, the penetration members 12 used in connection with the present disclosure may have generally vertical wall angles, i.e., the penetration members may be in the form of pins, with sidewalls that are largely orthogonal to the surface 26 from which they protrude. Further, although the penetration members 12 are shown with relatively smooth surfaces, it will be appreciated that surface(s) of the penetration members may be roughened, structured, etc., to enhance fluid flow over or through the penetration members.

In another aspect of the present disclosure, at least a portion of one or more penetration members 12 can include one or more detection reagents (not shown) and/or sensor elements (not shown) configured to detect one or more target analytes in the fluid leaked from a blood vessel (or blood vessels) comprising the dermis as a result of exposure to a laser beam. In some instances, the distal end 22 of a penetration member 12 can coated with one or more detection reagents. Where the device 10 comprises an array of penetration members 12, each of the penetration members can include the same or different detection reagent(s). In one example, certain penetration members 12 comprising an array can include a first detection reagent for detecting a first target analyte, while certain other penetration members can include a second different detection reagent for detecting a second different target analyte. Thus, in some instances, the devices 10 and systems of the present disclosure can be configured to detect multiple different target analytes.

In some instances, one or more penetration members 12 can include a sensor element for detecting a target analyte. A sensor element can be in electrical communication with a data component 32 of the device 10. In one example, a sensor element can be disposed on an outer surface of a penetration member 12. In another example, a sensor element can be disposed within the channel 28 of a penetration member 12 such that fluids traveling through the channel contact the sensor element. The sensor elements may be the same or different (e.g., sensor elements can be configured to detect the same or different target analytes). The sensor element may be used to sense any of a number of target analytes in the fluid leaked from a blood vessel comprising the dermis. In some constructions, the device 10 may be provided with an electrically conductive circuit pattern (not shown) to facilitate electrochemical analysis of the leaked fluid. Alternatively, the sensor element may be configured to undergo an optical change dependent upon detection of particular target analyte. Other alternative sensing techniques will be known to those of skill in the art.

In another aspect, devices 10 and systems of the present disclosure can include a laser source 14. In some instances, the laser source 14 can be configured to deliver a laser beam having a wavelength that excites at least one of hemoglobin and oxyhemoglobin present in a blood vessel (e.g., a capillary) comprising the dermis (e.g., the upper dermis). In one example, the laser source 14 can comprise a 532 nm Nd:YAG laser having a fluence of 1 J/cm$^2$ and an energy of 0.38 J. In another example, the laser beam can have a fluence of 7.5-20 J/cm$^2$ to induce rupture of one or more blood vessels comprising the dermis. In yet another example, the laser beam can have a fluence of about 4 J/cm$^2$ (e.g., 4 J/cm$^2$) to induce leakage, but not rupture, of one or more blood vessels comprising the dermis.

The laser beam can be continuous or pulsatile, and can be delivered to the dermis for a time sufficient to induce leakage or rupture of one or more blood vessels comprising the dermis. For example, the laser beam can have a pulse width of about 2 ns to about 10 ns (e.g., 5-7 ns). In some instances, the laser source 14 can be disposed within the housing 16 of the device 10 (FIG. 1A). In other instances, the laser source 14 can be located physically apart from the housing 16. As shown in FIG. 1B, for example, the laser source 14 can be located physically apart from the housing 16 except for an electrical connection (e.g., a fiber optic cable 30) sufficient to convey a laser beam to one or more penetration members 12 comprising the device 10. In other instances, the laser source 14 can be completely separate from the housing 16 so that the device 10 and the laser source are free from connection to one another.

In another aspect, devices 10 of the present disclosure can include one or more data components 32 for collecting, storing, analyzing, and/or displaying data generated upon detection of a target analyte (or analytes). The data component 32 can be in electrical communication with the laser source 14 and/or at least one penetration member 12. In some instances, a data component 32 can be disposed within the housing 16 of the device 10 (FIG. 1A). In other instances, a data component 32 can be located physically apart from the housing 16. As shown in FIG. 1B, for example, the data component 32 can be located physically apart from the housing 16 except for an electrical connection (e.g., a wire) that connects the data component to the laser source 14. In other instances, a data component 32 can be completely separate from the housing 16 so the data component is free from connection thereto. In such instances, the data component 32 can be in wireless communication with the laser source 14 and/or at least one penetration member 12. For example, the data component 32 can be in wireless communication with a cell phone (not shown) or other portable electronic device. In such instances, the cell phone can be used to monitor data generated by the data component 32 and/or provide instructions for operation of the device 10.

The data component 32 can comprise a memory (e.g., a non-transitory memory) storing computer-executable instructions and a processor to access the memory and execute the computer-executable instructions. In some instances, the processor can be configured to execute the computer-executable instructions to at least record data generated upon detection of one or more target analytes (e.g., a signal generated upon binding of a target analyte to a detection reagent), analyze the data, and display the data on a graphical user interface associated with the device 10. In some instances, the processor can be configured to execute the computer-executable instructions to control administration of an agent (e.g., through a penetration member 12) to the dermis of a subject. The processor can be any type of device (e.g., a central processing unit, a microprocessor, or the like) that can facilitate the execution of the computer-executable instructions to perform one or more actions of the actions listed above. The memory can include one or more non-transitory media (not a transitory signal) that can contain or store the program instructions for use by or in connection with storing and/or analyzing data generated upon detection of one or more target analytes. Examples (a non-exhaustive list) of non-transitory media can include: an electronic, magnetic, optical, electromagnetic, infrared, or semiconductor system, apparatus or device. More specific examples (a non-exhaustive list) of non-transitory media, which may or may not be directly connected to devices of the present disclosure, can include the following: a portable computer diskette; a random access memory; a read-only memory; an erasable programmable read-only memory (or Flash memory); and a portable compact disc read-only memory.

It will be appreciated that devices 10 of the present disclosure can include other components, such as a power source (not shown). For example, devices 10 of the present disclosure can include one or more external or internal power sources, such as a battery. The power source can be in electrical communication with any other components of the device 10, such as the laser source 14 and/or the data component 32. In some instances, a battery can be included within the housing 16 of a device 10. In other instances, a power source can be located external to the device 10 but remain in electrical communication with one or more components of the device (e.g., the laser source 14 and/or the data component 32).

Methods

Figure 3:
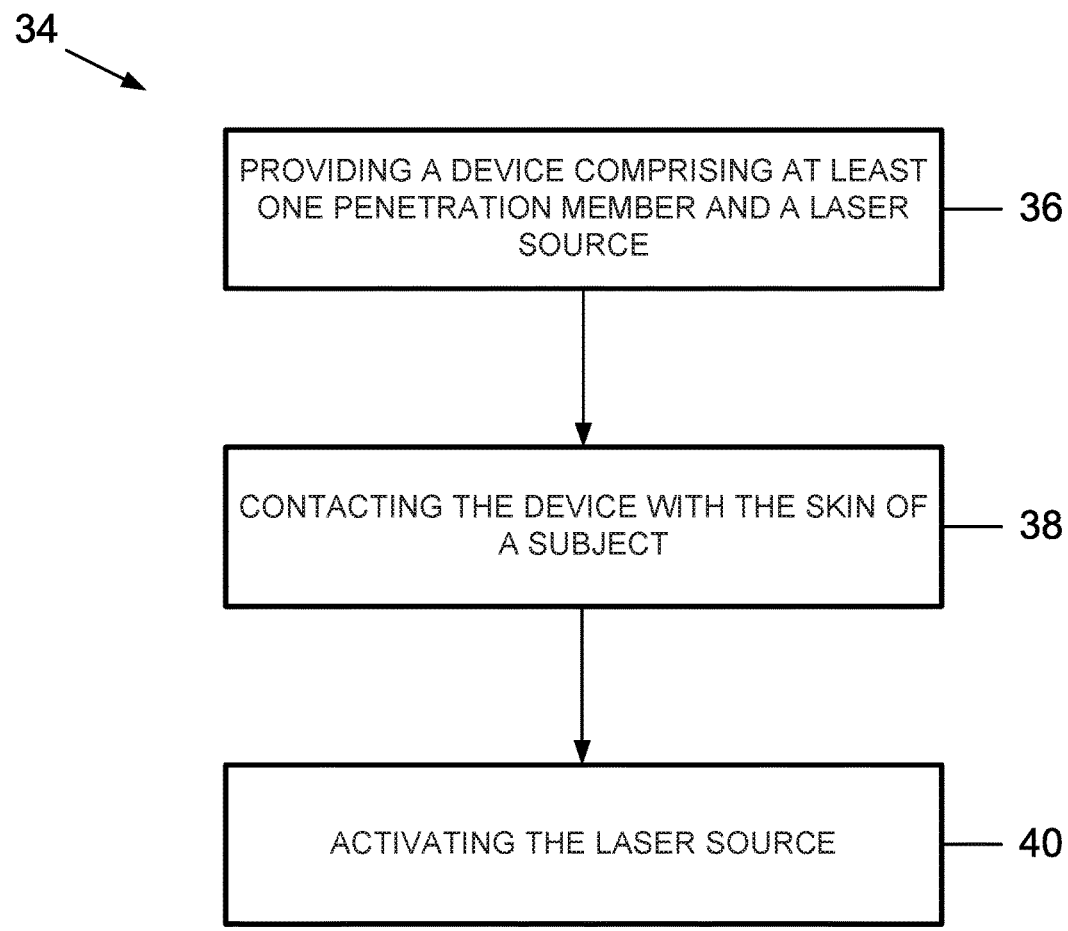
FIG. 3 is a process flow diagram illustrating a method for inducing leakage or rupture of a blood vessel comprising a dermis of a subject according to another aspect of the present disclosure.

Another aspect of the present disclosure can include a method 34 (FIG. 3) for inducing leakage or rupture of a blood vessel comprising the dermis of a subject. As shown in FIG. 3, the method 34 can include the steps of: providing a device comprising one or more penetration members that is coupled to a laser source (Step 36); contacting the device with the skin of a subject so that at least a distal end of the penetrating member(s) directly contact(s) the dermis (Step 38); and activating the laser source to deliver a laser beam to the dermis for a time sufficient to induce leakage or rupture of at least one blood vessel comprising the dermis (Step 40).

The device provided at Step 36 can be identically or similarly constructed as the devices 10 illustrated in FIGS. 1A-2B and described above. However, it will be appreciated that the device configuration can be modified or changed to account for numerous variables including, but not limited to, the general health of a subject, the age of the subject (e.g., pediatric or adult), the particular point-of-care or onsite environment, and the indication or end-point sought by the user (e.g., treatment, diagnosis, etc.).

At Step 38, all or only a part of the device 10 can be contacted with the skin of the subject. For example, one or more penetration members 12 of the device 10 can be contacted with the skin so that the housing 16, when depressed, causes the penetration member(s) to pierce the epidermis. It will be appreciated that the area of skin intended for contact with the device 10 can be prepped prior to contact (e.g., by applying a disinfectant and/or topical anesthetic). Further downward pressure can then be applied to the device 10 until the surface 26 is completely or substantially flush with the skin of the subject. In doing so, each of the penetration members 12 travels through the epidermis so that, ultimately, at least a portion of the distal end 22 of each penetration member is disposed in, and enveloped by, the dermis. In other words, at least a portion of the distal end 22 of each penetration member 12 is in direct contact with the dermis (e.g., the upper dermis). In some instances, only the entire distal end 22 is disposed in, and enveloped by, the dermis.

At Step 40, the laser source 14 can be activated to deliver a laser beam directly to the dermis. In some instances, the laser source 14 can be activated after Step 38. In other instances, the laser source 14 can be activated either before or during Step 38. The laser beam can be delivered to the dermis via the penetration member(s) 12. Alternatively, after Step 38, the device 10 can be removed from skin of the subject and the laser beam applied to the skin area containing pores (made by the device) so that the laser beam is delivered through the pores to the dermis. The laser beam can be delivered to the dermis (e.g., the upper dermis) under conditions (e.g., duration, pulse, power, and energy density) sufficient to induce leakage or rupture of at least a portion of one or more blood vessels (e.g., capillaries) comprising the dermis. In some instances, the laser beam can be delivered to the dermis (e.g., the upper dermis) under conditions (e.g., duration, pulse, power, and energy density) sufficient to induce leakage, but not rupture, of at least a portion of one or more blood vessels (e.g., capillaries) comprising the dermis. Whether or not the blood vessel(s) is/are ruptured at Step 40, or only caused to become leaky but without rupturing, will depend upon the parameters (e.g., duration, pulse, power, and energy density) of the laser beam applied to the dermis. This is due, at least in part, to the peak absorbance of hemoglobin and oxyhemoglobin (540 nm and 578 nm, respectively) present inside red blood cells. Thus, upon laser illumination at or near these wavelengths, abundant hemoglobin and oxyhemoglobin flowing inside the blood vessel(s) absorb laser energy into heat to partially or completely destroy the blood vessel(s) comprising the dermis. Advantageously, and as discussed further below, selective permeation or destruction of blood vessels comprising the dermis results in release of blood vessel contents into the surrounding dermal tissue and thereby permits a variety of subsequent diagnostic and therapeutic applications.

Another aspect of the present disclosure can include a method 42 (FIG. 4) for detecting a target analyte in a dermis of a subject. Currently, direct application of probe-coated microneedles into the skin is insufficient and unreliable for any diagnosis due to an extremely low level of blood biomarkers in the skin and uncharacteristic capillary damage occurring during microneedle application. As discussed below, the method 42 of the present disclosure can include application of a laser beam at a wavelength near the peak absorbance of hemoglobin and/or oxyhemoglobin to specifically induce vessel leakage beneath the epidermis, thereby resulting in a high level (1,000-fold increase) and even accumulation of circulating target analytes (or biomarkers) in the dermis (e.g., the upper dermis), which can be sufficiently and reliably captured by one or more penetration members 12 coated with one or more detection reagents (or probes). Thus, in some instances, the method 42 provides several advantages for blood analyte quantification, such as: (1) leakage of only circulating molecules, not cells, which mimics plasma processing and allows coated penetration members 12 to directly detect any target analytes in the skin with a high sensitivity; (2) detection of target analytes in the upper dermis instead of the deep dermis is minimally invasive and painless; (3) substantially reducing the measurement error from one test to another, making the method highly reliable for diagnosis due to even accumulation of target analytes at the site of penetration member application; and (4) allowing uniform capture of a specific target analytes on each coated penetration member in the same array, thus making it possible to accurately detect multiple target analytes in a single patch or array.

Figure 4:
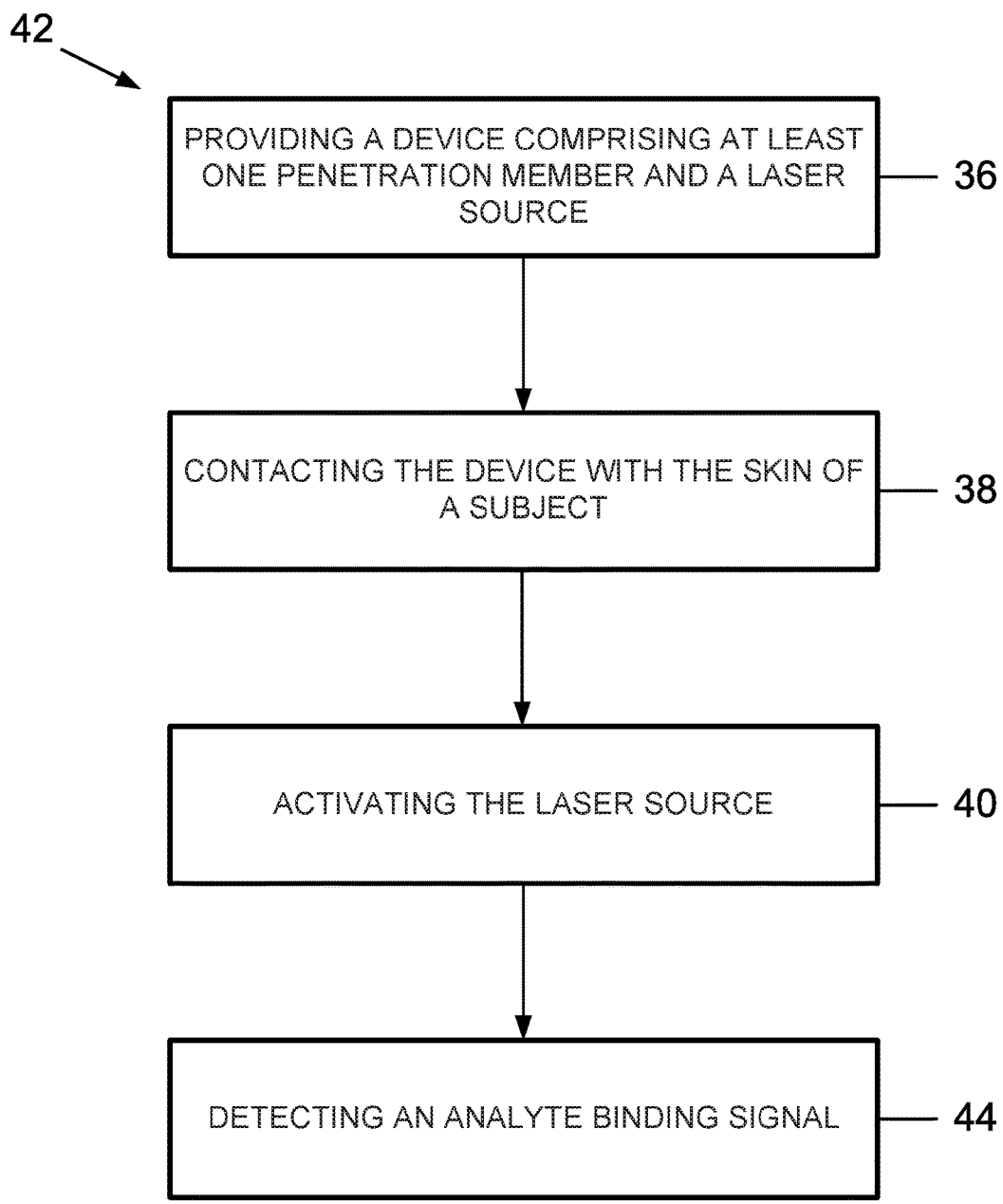
FIG. 4 is a process flow diagram illustrating a method for detecting a target analyte in a dermis of a subject according to another aspect of the present disclosure.

Referring to FIG. 4, Steps 36-40 of the method 42 can be identically or similarly performed as in the method 34 (FIG. 3) described above. Then, at Step 44 (FIG. 4), one or more target analytes, if present, in the fluid leaked from the blood vessel(s) can be detected. Detection can occur, for example, when a target analyte binds to a related detection reagent, thereby generating a detectable binding signal. In some instances, the detectable binding signal can be a visible or fluorescent signal. In other instances, the detectable binding signal can be a calorimetric change (e.g., detectable via a sensing element). The detected binding signal can then be converted (e.g., via the data component 32) to an electronic signal indicative of target analyte concentration. In some instances, the magnitude and temporal profile of the electronic signal can be indicative of target analyte concentration in the fluid leaked from the blood vessel. It will be appreciated that Step 44 can be repeated multiple times in order to increase the sensitivity of the method 42. Advantageously, the method 42 permits an efficient, safe, and convenient approach to detecting multiple target analytes in a single array, which can significantly reduce time and material costs associated with blood analyte diagnosis.

Figure 5:
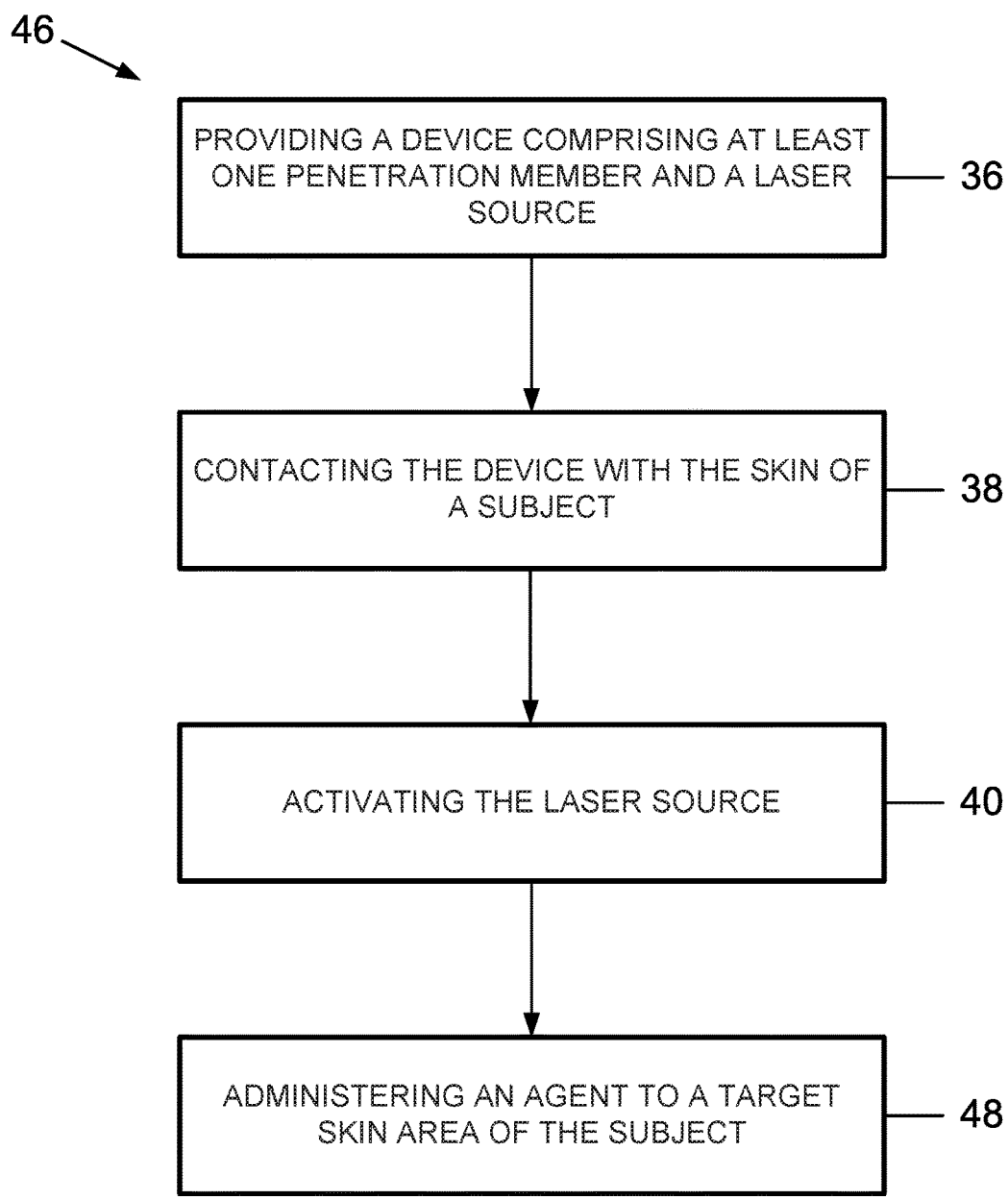
FIG. 5 is a process flow diagram illustrating a method for facilitating skin-to-blood delivery of an agent in a subject according to another aspect of the present disclosure.

Another aspect of the present disclosure can include a method 46 (FIG. 5) for facilitating skin-to-blood delivery of an agent in a subject. Referring to FIG. 5, Steps 36-40 of the method 46 can be identically or similarly performed as in the method 34 (FIG. 3) described above. Then, at Step 48 (FIG. 5), one or more agents can be administered to a target skin area of the subject. The target skin area can be defined by the portion of the subject's skin where the penetration member(s) 12 of the device 10 was/were applied to create one or more pores that extend through the epidermis into the dermis. The agent(s) can be delivered to the target skin area, and thus into the dermis, via intradermal injection, for example. In one example, intradermal injection can be done by flowing the agent(s) through the penetration member(s) 12 when the penetration member(s) is/are disposed within the dermis (e.g., immediately after Step 40). In this case, the device 10 can include an internal reservoir (not shown) containing the agent(s), which can be selectively activated (e.g., by a user) to dispense the agent(s). Alternatively, the reservoir of the agent(s) can be connected to the device 10 (e.g., via tubing) and then flowed therethrough into the penetration member(s) 12. In other instances, one or more agents can be directly administered to the target skin area using a hypodermic needle (or the like) following Step 40. Advantageously, the agent(s) administered to the target skin area, and thus the dermis, can readily enter and be taken up into the leaky blood vessels (created at Step 40), and thus the vasculature, of the subject. Not only does this decrease absorption time and the amount of agent(s) required to achieve a particular result, it also spares the dermal vasculature from permanent destruction, thereby reducing patient discomfort. The method 46 can find use in a variety of clinical applications including, but not limited to, therapeutic and imaging applications.

In one example, the method 46 can be used to vaccinate a subject for malaria. *Plasmodium falciparum* (Pf) parasite infects ~300 million people and causes ~1 million deaths a year. Yet, there is no an effective, licensed vaccine for prevention against this disease. Bites of irradiated (r), malaria-infected mosquitoes can confer sterile immune protection against this disease in both humans and animals; however, this approach faces formidable technical hurdles in the clinic because immunization of a large number of people by bites of infected mosquitoes is both impractical and unethical. For sporozoites (rSPZs)-based vaccines, the number of rSPZs trafficking to the liver is critical in induction of sterilizing immunity against malaria since the liver is the only organ supporting synthesis of liver stage-specific antigens that, along with SPZs, are major determinants for stimulating protective immunity. Intravenous (IV) injection is the most efficient means in delivering SPZs to the liver, but it is not a clinically-approved route of immunization. On the other hand, intradermal (ID) vaccination, though mimicking natural infection and also a clinically acceptable route, is 3-5 times less efficient than IV because emigration of SPZs out of the skin is highly restricted by the densely packed connective tissue network in the dermis. The efficiency may particularly be an issue for cryopreserved rSPZs as these cryopreserved rSPZs display reduced motility.

The inventor has surprisingly found that laser pre-illumination of the inoculation site prior to ID increased skin-to-liver traffic of ySPZs to a level comparable to IV injection. The laser illumination specifically injures the blood vessels or capillary while sparing the surrounding tissues from laser-mediated damage. Advantageously, application of the method 46 causes the injured blood vessels or capillaries to "open" for SPZ entrance into blood vessels, via which the ID-injected SPZs can travel into the liver and initiate a highly potent immune response for effective vaccination.

It will be appreciated that the method 46 can also be used to induce immune tolerance, control of cancer metastasis, and boost immune responses.

Figure 6:
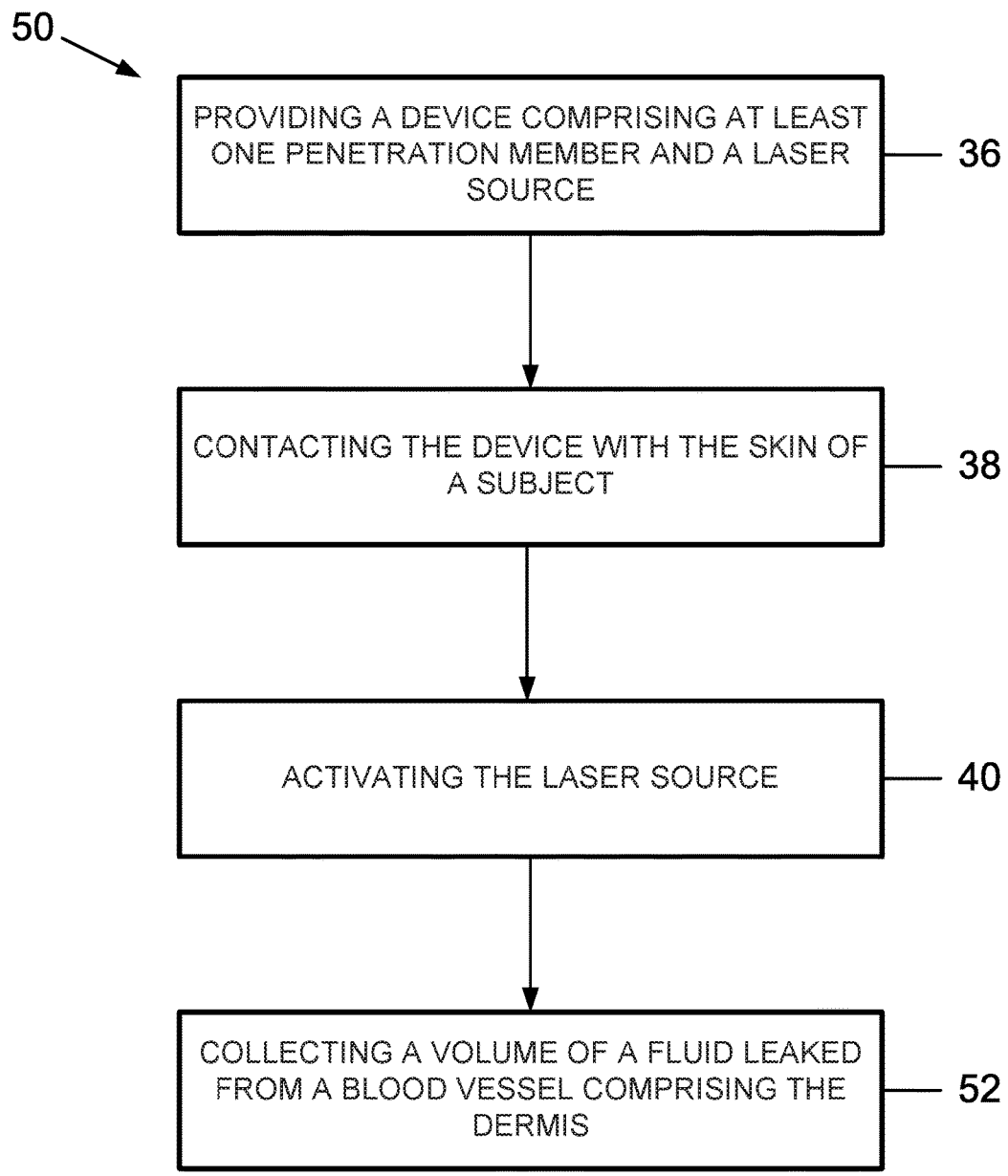
FIG. 6 is a process flow diagram illustrating a method for collecting a fluid sample from a dermis of a subject according to another aspect of the present disclosure.

Another aspect of the present disclosure can include a method 50 (FIG. 6) for collecting a fluid sample from the dermis of a subject. Referring to FIG. 6, Steps 36-40 of the method 50 can be identically or similarly performed as in the method 34 (FIG. 3) described above. Then, at Step 52 (FIG. 6), a volume of a fluid leaked or released from the at least one blood vessel comprising the dermis can be collected. Depending upon whether the blood vessel(s) was/were completely ruptured, or only induced to leak (but not rupture), the fluid leaked or released from the blood vessel(s) can contain one or more target analytes, including cells (e.g., where the blood vessel(s) was/were completely ruptured). In some instances, the fluid sample can be collected by suctioning fluid through one or more of the penetration members 12 comprising the device 10. Suction can be applied where, for example, the device 10 includes an integrated suction mechanism (e.g., a plunger or a pump) (not shown) that can be selectively activated by a user. Alternatively, an external suction mechanism can be connected to the device 10 and then activated when fluid removal is desired. In other instances, the fluid sample can be collected using a device (e.g., a syringe) or suction mechanism other than the device 10 of the present disclosure. After Step 40, for example, the device 10 can be removed from the skin of the subject, whereafter a syringe or other suction mechanism is applied to the target skin area to collect the fluid sample. Fluid collected by the method 50 can then be analyzed (e.g., assayed) for the presence of one or more target analyses using analysis techniques (e.g., ELISA) known to those of skill in the art. Advantageously, the method 50 permits relatively painless and efficient collection of vascular fluid without the need to perform conventional intravenous blood draws.

Figure 7:
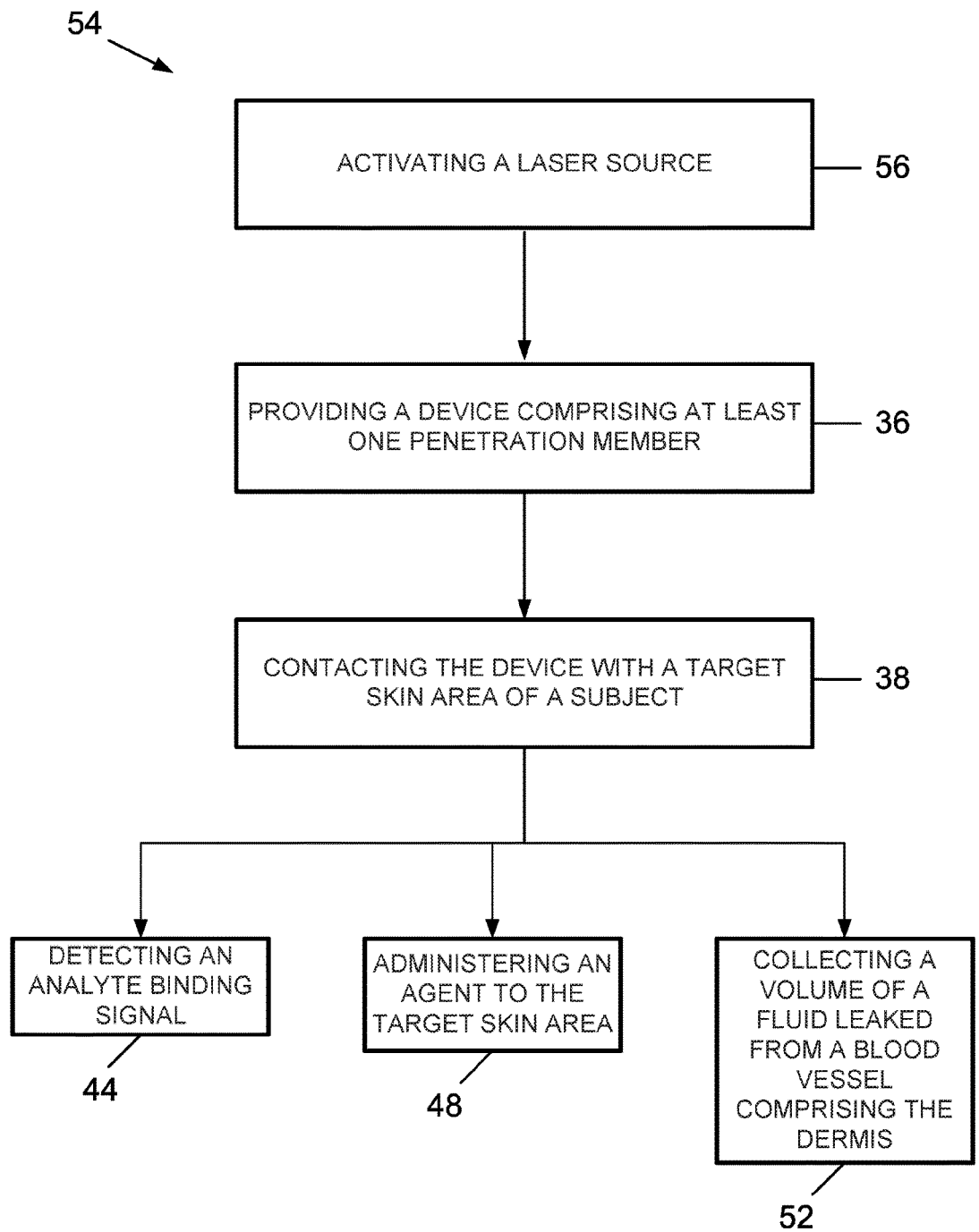
FIG. 7 is a process flow diagram illustrating an alternative method for inducing leakage or rupture of a blood vessel comprising a dermis of a subject according to another aspect of the present disclosure.

Another aspect of the present disclosure can include a method 54 (FIG. 7) for inducing leakage or rupture of a blood vessel comprising the dermis of a subject. As shown in FIG. 7, the method 54 can include the steps of: activating a laser source to deliver a laser beam to the dermis for a time sufficient to induce leakage or rupture of at least one blood vessel comprising the dermis (Step 56); providing a device comprising one or more penetration members (Step 36); and contacting the device with a target skin area of a subject so that at least a distal end of the penetrating member(s) directly contact(s) the dermis (Step 38). Further optional Steps of the method 54 are discussed below.

Prior to Step 56, a laser source 14 can be positioned adjacent (e.g., directly adjacent) a target skin area of the subject at a desired distance. In some instances, the desired distance can be less than about 1 cm, about 1 cm, about 1-2 cm, about 2-3 cm, about 3-4 cm, about 4-5 cm, about 5-6 cm, about 6-7 cm, about 7-8 cm, about 8-9 cm, about 9-10 cm, or more. In other instances, a light-emitting portion of the laser source 14 can be directly contacted with the target skin area of the subject.

At Step 56, the laser source 14 can be activated to deliver a laser beam directly to the dermis. The laser beam can be delivered to the dermis (e.g., the upper dermis) under conditions (e.g., duration, pulse, power, and energy density) sufficient to induce leakage or rupture of at least a portion of one or more blood vessels (e.g., capillaries) comprising the dermis. In some instances, the laser beam can be delivered to the dermis (e.g., the upper dermis) under conditions (e.g., duration, pulse, power, and energy density) sufficient to induce leakage, but not rupture, of at least a portion of one or more blood vessels (e.g., capillaries) comprising the dermis. Whether or not the blood vessel(s) is/are ruptured at Step 56, or only caused to become leaky but without rupturing, will depend upon the parameters (e.g., duration, pulse, power, and energy density) of the laser beam applied to the dermis. This is due, at least in part, to the peak absorbance of hemoglobin and oxyhemoglobin (538 nm and 578 nm, respectively) present inside red blood cells. Thus, upon laser illumination at or near these wavelengths, abundant hemoglobin and oxyhemoglobin flowing inside the blood vessel(s) absorb laser energy into heat to dilate or partially or completely destroy the blood vessel(s) comprising the dermis. Advantageously, and as discussed above, selective permeation or destruction of blood vessels comprising the dermis results in release of blood vessel contents into the surrounding dermal tissue and thereby permits a variety of subsequent diagnostic and therapeutic applications.

Following Step 56, a device 10 comprising at least one penetration member 12 can be provided (Step 36). The device provided at Step 36 can be identically or similarly constructed as the devices 10 illustrated in FIGS. 1A-2B and described above. However, as discussed above, it will be appreciated that the device configuration can be modified or changed to account for numerous variables including, but not limited to, the general health of a subject, the age of the subject (e.g., pediatric or adult), the particular point-of-care or onsite environment, and the indication or end-point sought by the user (e.g., treatment, diagnosis, etc.).

At Step 38, all or only a part of the device 10 can be contacted with the target skin area of the subject. For example, one or more penetration members 12 of the device 10 can be contacted with the target skin area so that the housing 16, when depressed, causes the penetration member(s) to pierce the epidermis. It will be appreciated that the target skin area can be prepped prior to contact (e.g., by applying a disinfectant and/or topical anesthetic). Further downward pressure can then be applied to the device 10 until the surface 26 is completely or substantially flush with the target area. In doing so, each of the penetration members 12 travels through the epidermis so that, ultimately, at least a portion of the distal end 22 of each penetration member is disposed in, and enveloped by, the dermis. In other words, at least a portion of the distal end 22 of each penetration member 12 is in direct contact with the dermis (e.g., the upper dermis). In some instances, only the entire distal end 22 is disposed in, and enveloped by, the dermis.

Following Step 38, any one or combination of Steps 44, 48, and 52 can be carried out as described above. To detect a target analyte present in a fluid leaked from the at least one blood vessel, for example, one or more target analytes (if present) in the fluid leaked from the blood vessel(s) can be detected at Step 44. Detection can occur, for example, when a target analyte binds to a related detection reagent, thereby generating a detectable binding signal. In some instances, the detectable binding signal can be a visible or fluorescent signal. In other instances, the detectable binding signal can be a calorimetric change (e.g., detectable via a sensing element). The detected binding signal can then be converted (e.g., via the data component 32) to an electronic signal indicative of target analyte concentration. In some instances, the magnitude and temporal profile of the electronic signal can be indicative of target analyte concentration in the fluid leaked from the blood vessel. It will be appreciated that Step 44 can be repeated multiple times in order to increase detection sensitivity.

Additionally or optionally, at Step 48, an agent can be administered to the target skin area following Step 38. In such instances, the agent can be administered to the target skin area as described above for FIG. 5. In other instances, it will be appreciated that an agent can be administered to the target skin area immediately following Step 56; that is, without having performed Steps 36-38 on the target skin area. In such instances, the target skin area can be defined as the portion of the subject's skin where the laser beam was applied at Step 56. Thus, after Step 56, one or more agents can be directly administered (e.g., via intradermal injection) to the target skin area using a hypodermic needle (or the like).

Additionally or optionally, at Step 52, a volume of a fluid leaked from a blood vessel comprising the dermis can be collected following Step 38. For example, depending upon whether the blood vessel(s) was/were completely ruptured, or only induced to leak (but not rupture), the fluid leaked or released from the blood vessel(s) can contain one or more target analytes, including cells (e.g., where the blood vessel(s) was/were completely ruptured). In some instances, the fluid sample can be collected by suctioning fluid through one or more of the penetration members 12 comprising the device 10. Suction can be applied where, for example, the device 10 includes an integrated suction mechanism (e.g., a plunger or a pump) (not shown) that can be selectively activated by a user. Alternatively, an external suction mechanism can be connected to the device 10 and then activated when fluid removal is desired. In other instances, the fluid sample can be collected using a device (e.g., a syringe) or suction mechanism other than the device 10 of the present disclosure. After Step 38, for example, the device 10 can be removed from the skin of the subject, whereafter a syringe or other suction mechanism is applied to the target skin area to collect the fluid sample. Collected fluid can then be analyzed (e.g., assayed) for the presence of one or more target analyses using analysis techniques (e.g., ELISA) known to those of skill in the art.

The following examples are for the purpose of illustration only and are not intended to limit the scope of the claims, which are appended hereto.

EXAMPLE 1

Conventional surface modified microneedle (MN) arrays inefficiently and unreliably capture circulating biomarkers from the skin and, thus, limit their clinical applications. In Example 1, the inventor surprisingly found that illumination of a tiny area of the skin with hemoglobin-preferably absorbent laser increased the amount of circulating biomarkers in the upper dermis by more than 1000-fold. The hemoglobin-specific light altered the permeability of capillaries leading to extravasation of molecules but not blood cells beneath the skin involved. When specific probe-coated MN arrays were applied into the laser-treated skin, the biomarkers accumulated in the upper dermis were reliably, accurately, and sufficiently captured as early as 15 minutes of the assay. The maximal binding occurred in 1 h in a manner independent of penetration depth or a molecular mass of the biomarker. With anti-fluorescein isothiocyanate (FITC)-MNs, the inventor was able to measure blood concentrations of FITC in mice receiving FITC intravenously. The sensitivity and accuracy were comparable to those attained by fluorescence spectrophotometer. Likewise, MNs containing influenza hemagglutinin (HA) could detect anti-HA antibody in mice or swine receiving influenza vaccines as effectively as standard immunoassays.

Materials and Methods
Materials

A heterobifunctional polyethylene glycol linker of 5 kDa, referred to as COOH-PEG-SH, was purchased from JenKem Technology (Allen, Tex., USA); 1-Ethyl-3-(3-dimethyl-amino-propyl) carbodiimide (EDC), N-hydroxysuccinimide (NHS), fluorescein isothiocyanate (FITC), gold chloride trihydrate, and ovalbumin (OVA) from Sigma Aldrich; and sylgard 184 elastomer from Dow Corning (Midland, Mich., USA). Influenza hemagglutinin (HA) protein from A/PR/8/34 strain was obtained from BEI resources, SU-8 2150 epoxy-based negative photoresist from MicroChem (Newton, Mass., USA), and polyclonal rabbit anti-FITC antibody and normal control rabbit IgG from Life Technologies (Frederick, Md., USA). FITC-conjugated secondary antibodies against mouse IgG or pig IgG were acquired from BioLegend (San Diego, Calif., USA) or Sigma (St. Louis, Mo., USA) respectively. Inactivated influenza vaccine was made by treatment of purified A/PR/8/34 virus with 0.024% formaldehyde at 4° C. for 1 week as previously described (Wang, J. et al., *Proc. Natl. Acad. Sci. U.S.A.* 112:5005-5010, 2015). The amount of HA protein in the vaccine was quantified by SDS-PAGE following a standard procedure.

Fabrication and Characterization of MNs

A female MNs mold was fabricated using a soft lithographic process. Briefly, a 1 mm thick SU-8 layer was spin-coated onto a freshly treated Si wafer, baked for 10 h, and then exposed to ultraviolet light (365 nm, 10 W/cm$^2$) at an angle of 20° and 10 rpm for 600 s through the dots patterning photomask that was placed on the surface of light-sensitive SU-8 layer, followed by baking for 2 h (Yang, S Y et al., *Nat. Commun.* 4:1702, 2013). A female MNs mold was formed after developing the SU-8 mold in propylene glycol methyl ether acetate for 6 h. To increase surface hydrophobicity of the conical cavities, trichloro (1H, 1H, 2H, 2H-perfluorooctyl) silane or fluorosilane was gas-phase deposited onto the surface. The base and curing agent of PDMS were then mixed at a ratio of 1:10 and cast into the SU-8 mold. After being degassed and cured at 95° C., the newly formed PDMS MN array was peeled off, treated with fluorosilane again, and used to generate another female PDMS MNs mold following a similar procedure. The second female MNs mold was cast with biocompatible epoxy-based resin, creating MNs with greater mechanical strength than PDMS MNs. MN arrays with 30 mm and 100 mm in lengths for mice or 250 mm and 500 mm for pigs were fabricated similarly. The resultant MNs were sprayed with chrome, forming a 20 nm adhesion layer on which 100 nm gold was coated as described (Jin, J. et al., *Adv. Healthc. Mater.* 3:349-353, 2014). The heterobifunctional linker COOH-PEG-SH was immobilized on the surface of gold-coated MNs via its SH group per the manufacturer's instruction (Muller, D A et al., *Anal. Chem.* 84:3262-3268, 2012). The linker not only reduced non-specific binding but also provided an anchor for capturing biomarkers. Rabbit anti-FITC or control antibody at 10 mg/mL, or HA or ovalbumin protein at 100 mg/mL, was used to covalently attach to the COOH of the linker in a standard EDC/NHS chemical reaction. The resultant MNs were rinsed 3 times with 0.05% Tween-20 in PBS to remove noncovalently bound antibodies or proteins and stored at 4° C. in PBS (Yeow, B. et al., *Anal. Chem.* 85:10196-10204, 2013; Corrie, S R et al., *Lab Chip* 10:2655-2658, 2010).

Specific Binding and Quantification of the Modified MNs

MN arrays coated with rabbit anti-FITC or control antibody were incubated with skimmed milk at 36° C. for 1 h to block non-specific binding, and then washed three times each for 1 min. The antibody-coated MN arrays were incubated at 36° C. with varying concentrations of FITC in 2% bovine serum albumin (BSA) in PBS (pH 6.8) for 2 h, or 2.5 mM FITC for indicated times. Photos of resulting MN arrays were captured by fluorescence microscopy, and the fluorescence intensity on each MN was analyzed by image J software (Corrie, S R et al., 2010). In a separate study, sera were prepared from naive mice or mice immunized intra-muscularly with 50 mL inactivated influenza vaccine (1 mg HA/mouse) for 4 weeks. HA-MNs, OVA-MNs, or uncoated MNs were immersed for 30 min at 1:300 dilutions for immunized serum or 1:100 for serum from naive mice. After thorough washing, the MNs were incubated with FITC-conjugated anti-mouse IgG and FITC intensities of individual MNs were measured as above. The amount of anti-HA IgG captured on the MNs was estimated by a standard curve run in parallel.

Laser-induced Extravasation in the Skin

To enhance circulating biomarkers in the upper dermis or epidermis, about 1 cm$^2$ of the lower dorsal skin of Balb/c mice (Charles River Laboratories, Wilmington, Mass.) was hair removed and illuminated the next day by a 532 nm pulse Nd:YAG laser with a beam diameter 7 mm, pulse width 7 ns, at a fluence of 0.5 J/cm$^2$ (UP-6G model, RMI Laser, LLC). FITC or Evans blue dye at indicated amounts was intravenously administered via a tail vein prior laser illumination. Extravasation of FITC or Evans blue dye at laser-treated site was tracked by intravital two photon confocal microscopy (Olympus FV-1000) before laser illumination and at varying times afterward. The skin tissue samples were also harvested for standard hematoxylin and eosin staining and histological evaluation, for fluorescence intensity measurement after cryosectioning, or for extraction of Evans blue dye. To study laser-induced extravasation in pigs, male Yorkshire pigs at 4 months of age and about 30 kg were obtained from the Teaching and Research Resources at Tufts University. The lower dorsal skin of the pigs was illuminated with a clinical, long pulse 595 nm laser with a beam diameter 7 mm, pulse width 0.45 ms, at a fluence of 4 $J/cm^2$ after 20 mL Evans blue dye at 2 mg/mL was i.v. administered via an auricular vein. Evans blue dye leakage in the skin was visualized by naked eye and skin photos were taken at indicated times after laser treatment to assess skin reaction and leakage of Evans blue dye at laser-treated sites.

Measurement of Circulating Biomarkers

To capture circulating FITC in the skin, Balb/c mice were i.v. injected with varying amounts of FITC, followed by laser illumination of the site of MN array application as above. Anti-FITC or control antibody-coated MNs were applied into laser-treated site or non-laser treated site for indicated times, after which the patches were removed, washed, and analyzed as above. Similarly, HA-MNs and OVA-MNs with two different lengths were applied into skin treated with either laser or sham light as above in mice that had received inactivated influenza vaccine 4 weeks ago. After 30 min application in the skin, the MN patches were carefully removed, transferred to a 96-well plate, and washed thoroughly. To the MNs containing plates, FITC-conjugated secondary antibody was added and incubated for an additional hour at room temperature, followed by washes. FITC intensity on each MN in the array was analyzed as above. Measurement of circulating anti-HA IgG in pigs was conducted similarly except that patches containing longer MNs, 250 mm and 500 mm, were employed in the skin for only 15 minutes. Two weeks before testing, the pigs were immunized with inactivated influenza vaccine at a dose of 2 mg HA/pig via intradermal injection. The amount of anti-HA IgG captured on the MNs was quantified on the basis of a standard curve generated by immunofluorescence (IF) assays of purified anti-HA antibody. The amounts of anti-HA IgG in the circulation was calculated by a formula: the amount of anti-HA IgG on the MNs÷skin tissue weight x a tissue dilution factor that was 10.9 in mice or 15.7 in pigs, corresponding to a difference in Evans blue concentrations between laser-treated skin and blood.

Immunofluorescence (IF) Assays

For quantification of anti-HA IgG, anti-HA IgG antibody was first purified from immunized pigs or mice as a standard. To purify the protein, sera were collected from the animals and passed through an HA protein affinity column that was made by a covalent linkage of HA's COOH group with the activated NHS in agarose resin (Thermo Pierce) in a standard EDC/NHS chemical reaction. The purity of the resultant anti-HA IgG was verified by SDS-PAGE and the amount of purified anti-HA IgG was quantified in the basis of the absorbance at 280 nm and stored at 4° C. (Wang, J. et al., 2011). The anti-HA IgG standard at a series of dilutions, along with immunized and control sera diluted similarly, were added in triplicate into a high protein binding black 96-well plate with clear flat bottom, which had been coated with HA protein overnight at 4° C. The resultant plate was incubated with skimmed milk for 1 h, and then with FITC-conjugated anti-mouse or pig IgG. Fluorescence intensity in each well was measured by fluorescence microplate reader after washes. The amount of anti-HA IgG in the serum was determined based on FITC intensity and the standard curve. Serum of immunized pigs or mice was collected just before the MNs were applied into the skin. Control serum was collected prior immunization.

Statistical Analysis

The difference between two groups was analyzed by two tailed t-test. One way ANOVA was used among multiple groups. P value was calculated by PRISM software (GraphPad, Calif.) and the statistical significance is indicated by *P<0.05, P<0.01 and *P<0.001.

Results

FITC Capture by Anti-FITC Antibody-coated MNs

Figure 8:
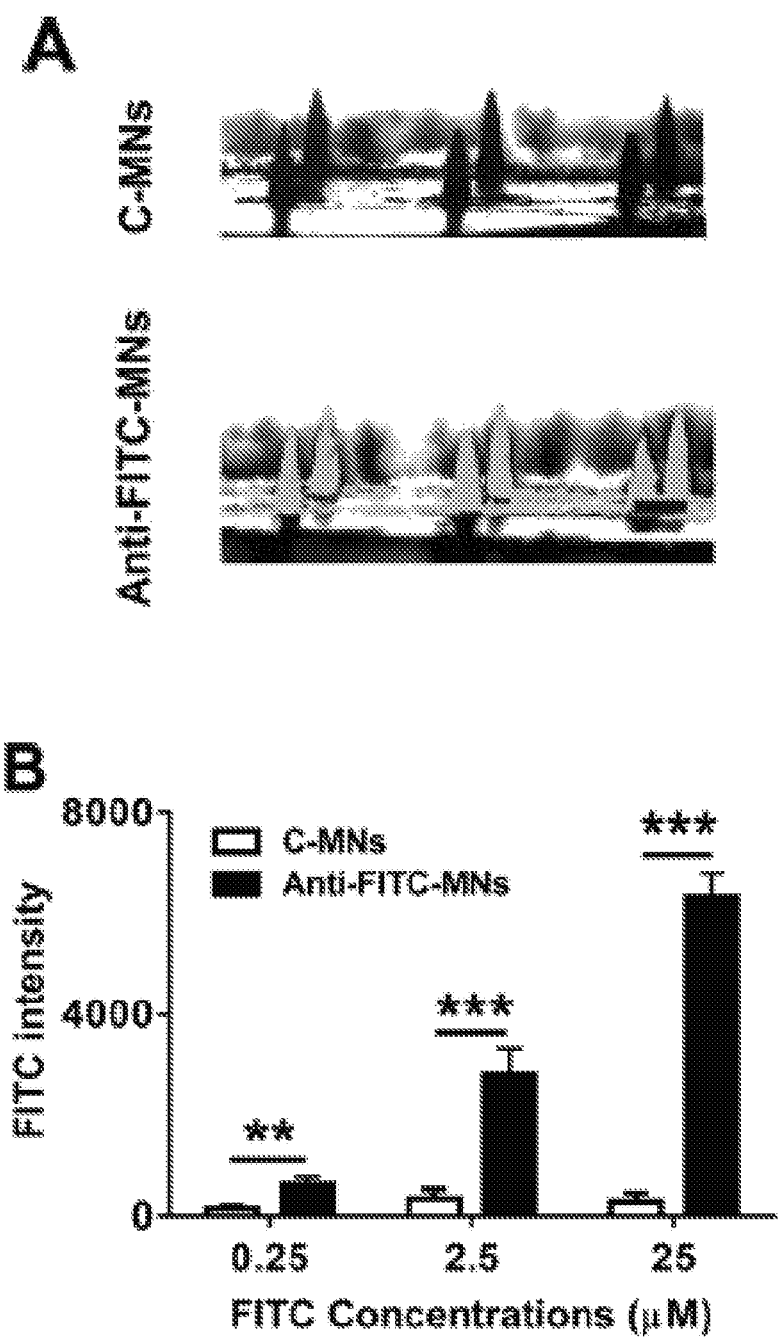
FIGS. 8A-D illustrate FITC measurement in vitro and in vivo by anti-FITC MNs.
Figure 8:
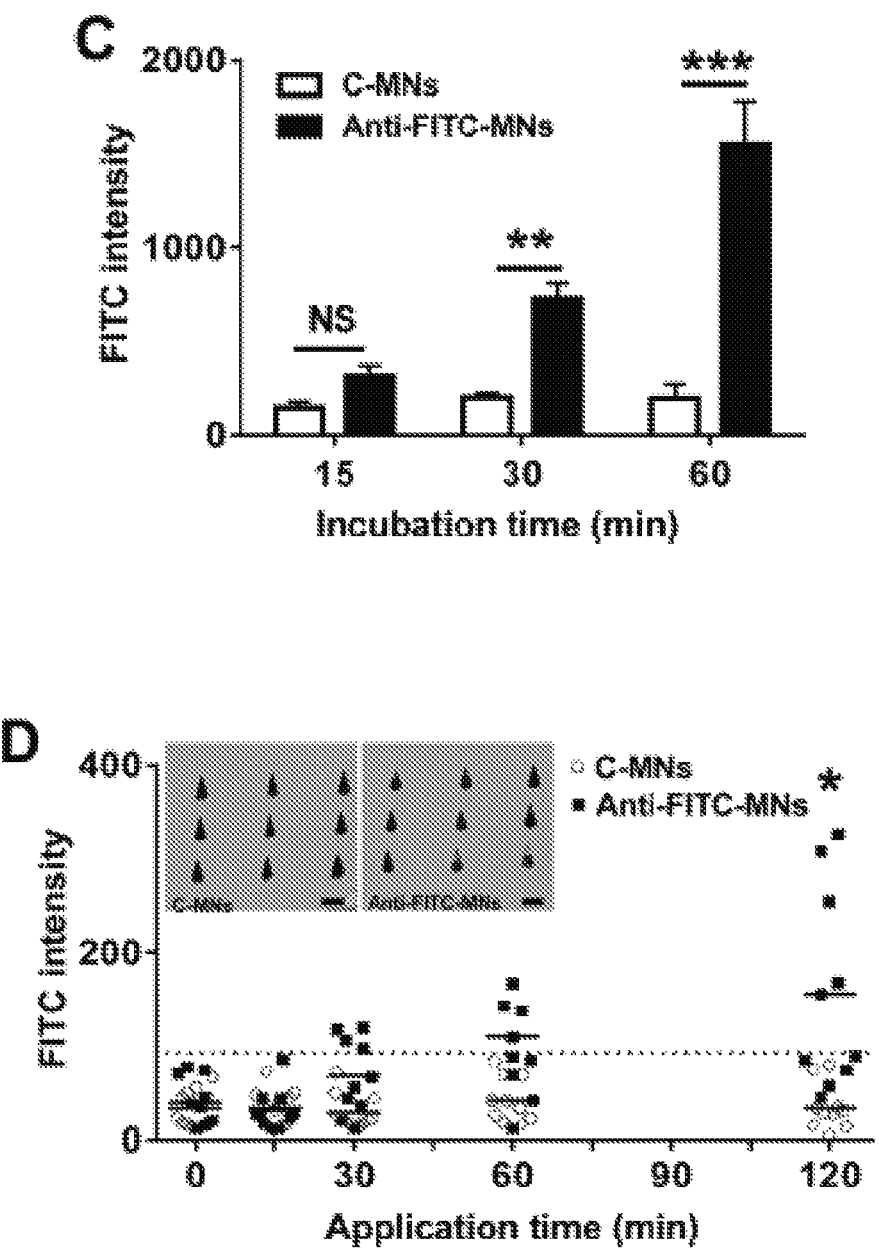

Anti-FITC antibody-coated MNs (anti-FITC-MNs) and control antibody-coated MNs (C-MNs) were prepared in arrays that each included 9 MNs as reported (Yang, S Y et al., 2013; Xiang, Z. et al., *Biomicrofluidics* 7:66501, 2013). They were then incubated with FITC at concentrations ranging from 0.25 to 25 mM for 2 h at 36° C., a temperature corresponding to that of skin. Photos of resulting MNs under a fluorescence microscope confirmed specific FITC binding of the MNs (FIG. 8A), as fluorescence was uniformly presented on anti-FITC-MNs but not on C-MNs. The fluorescence intensity of each MN was then quantified by Image J, and a mean intensity of each array was correlated to FITC concentrations (FIG. 8B). The intensity also increased proportionally to length of incubation (FIG. 8C).

Figure 14:
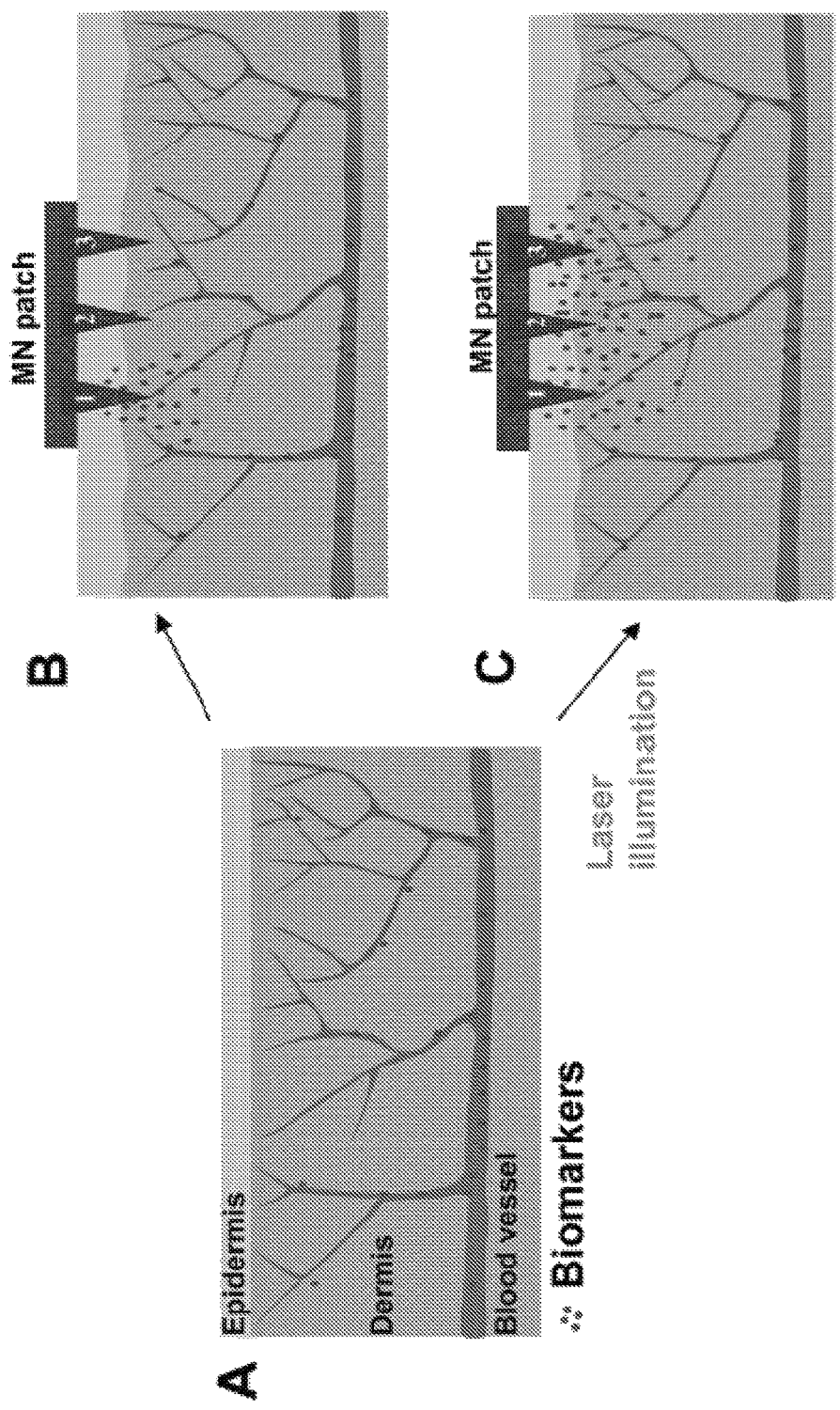
FIGS. 14A-C are schematic illustrations of differences in distribution and concentration of circulating biomarkers in laser-treated and non-treated skins.

When 100 mm MN were inserted into the dorsal skin of mice receiving 100 mL FITC at 4 mg/mL, no C-MN arrays reached fluorescent intensity above the cutoff line after 2 h in the skin (FIG. 8D). On the other hand, a few anti-FITC-MN arrays exceeded the cutoff value after 30 min, but the mean intensity did not exceed cutoff until 1 h into the experiment (FIG. 8D), and even then statistical analysis indicated an insignificant difference in the intensity between control and anti-FITC-MN arrays. Thus, by this method anti-FITC-MNs only captured FITC above background at a statistically significant level by the 2 h mark (FIG. 8D). Yet, there were large variations in intensity by this point, such that only 5 of 10 arrays were above the cutoff line. These variations apparently resulted from FITC unevenly captured on some MNs in the array. Among the 9 MNs in the inset of FIG. 8D, 2 MNs displayed strong FITC binding, 3 had weak interactions, and 4 exhibited no FITC binding at all. The uneven FITC binding was presumably caused by uncharacterized capillary damage around individual MNs during MN penetration, since in vitro assays confirm a uniform FITC binding in all MNs in the array (FIG. 8A). As depicted in FIG. 14B, high FITC binding may occur only on an MN that is physically at or close to the site of capillary damage such as MN #1, but not on an MN that is physically away from the site such as MN #3.

Laser Induces Controllable Extravasation

Figure 9:
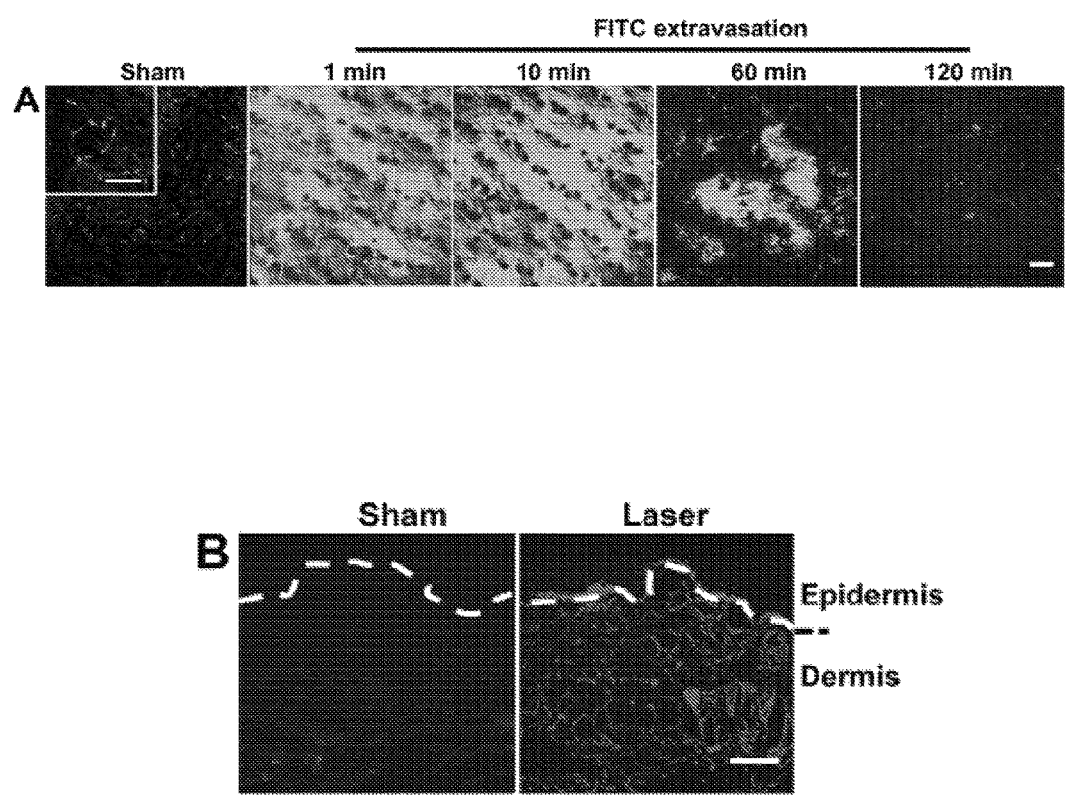
FIGS. 9A-D illustrate laser induction of extravasation.
Figure 9:
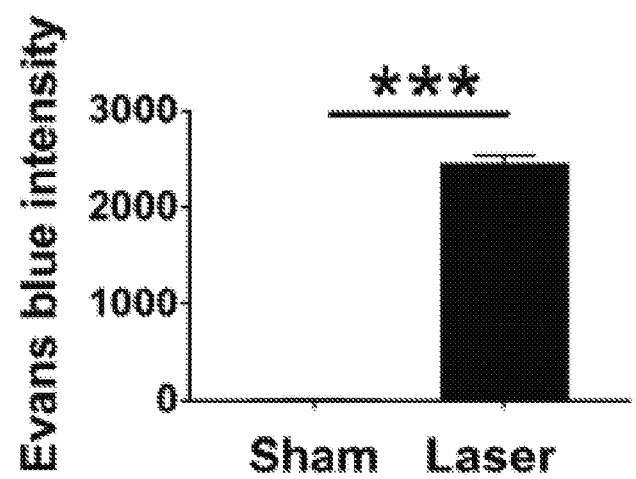
Figure 9:
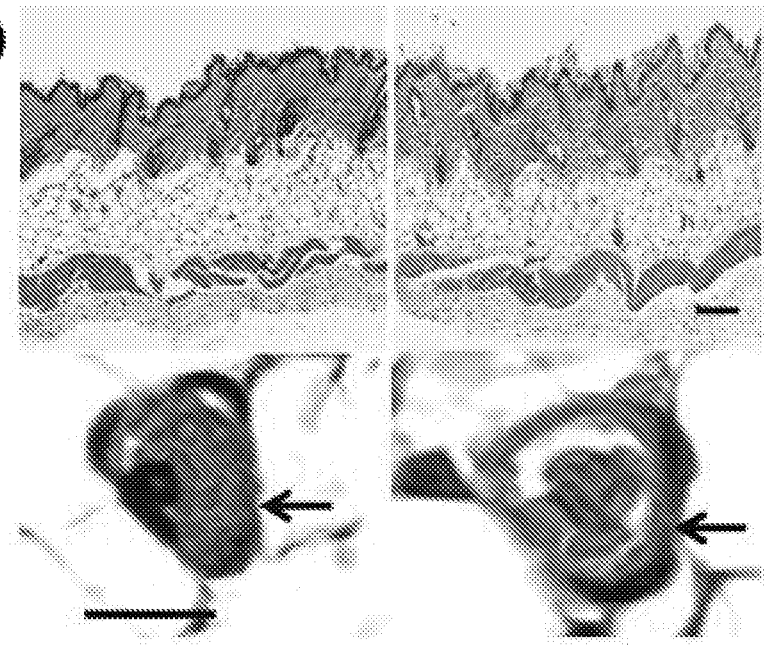

Having conducted a series of pilot studies with various lasers at different energy densities, we found that a 532 nm pulse Nd:YAG laser (NYL) could trigger extravasation of the capillary beneath the skin after 5 s illumination, without incurring any damage to the surrounding tissues. Briefly, the lower dorsal skin of mice was hair removed and illuminated by NYL laser for 5 s with a beam diameter 7 mm and pulse width 7 ns at 0.5 $J/cm^2$ after intravenous injection with 100 mL FITC at 4 mg/mL. The illumination site was subjected to analysis with two photo confocal laser scanning microscopy at indicated times. Prior laser illumination, capillary network was clearly visible by fluorescent labeling, as FITC was well confined within the microvessels on a high magnification (FIG. 9A, the upper left in the first panel). Upon illumination, FITC leakage was seen immediately, quickly accumulating in the skin tissue within 1 min (FIG. 9A), reaching a maximal level in 10 min. The strong fluorescence was sustained for 10-20 min, subsided gradually thereafter, diminished substantially in 1 h, and completely disappeared in 2 h (FIG. 9A). Laser-induced capillary permeability was also verified using Evans blue dye, which binds albumin in the bloodstream and becomes impermeable to blood vessels after intravenous injection. Evans blue could be seen in the skin immediately after laser illumination by naked eye, reached a maximal level in 15 min, and completely resolved in 2 h. Besides its visible blue color, Evans blue is also a red fluorescent dye with an excitation at 620 nm and emission at 680 nm. Under a fluorescent microscope, Evans red fluorescence was seen throughout the dermis, and in particular a bright fluorescence was presented in the upper dermis in laser treated skin, in marked contrast to non-laser-treated skin where there was dim fluorescence in the dermis and little in the supper dermis (FIG. 9B). The fluorescence intensity in the upper dermis was more than 1000-fold higher in the presence than in the absence of laser illumination as analyzed by Image J (FIG. 9C). When laser treated skin with dimensions of 5×5 $mm^2$ and 500 mm depth was dissected 10 min after illumination, Evans blue was extracted from the skin and measured by fluorescence spectrophotometer, yielding 7.3 mg/mL of the dye in the skin. In comparison to a concentration in serum (80.1 mg/mL), Evans blue was diluted by ~11-fold in skin tissue. The factor of skin tissue dilution was subsequently used to calibrate skin measurement of blood biomarkers. Likewise, we determined a tissue dilution factor of 3 for FITC under similar laser treatment, much less than Evans blue-albumin, probably because the smaller size of FITCs allows for rapid diffusion from vessels and accumulation in the skin. The data suggests that a tissue dilution factor must be taken into consideration when a biomarker detected in the skin is correlated with its blood concentration. As a final remark, while inducing significant extravasation, no significant alteration was found histologically in laser-treated skin as compared to non-laser-treated control, except for slight capillary dilation in laser-treated skin (FIG. 9D).

Figure 10:
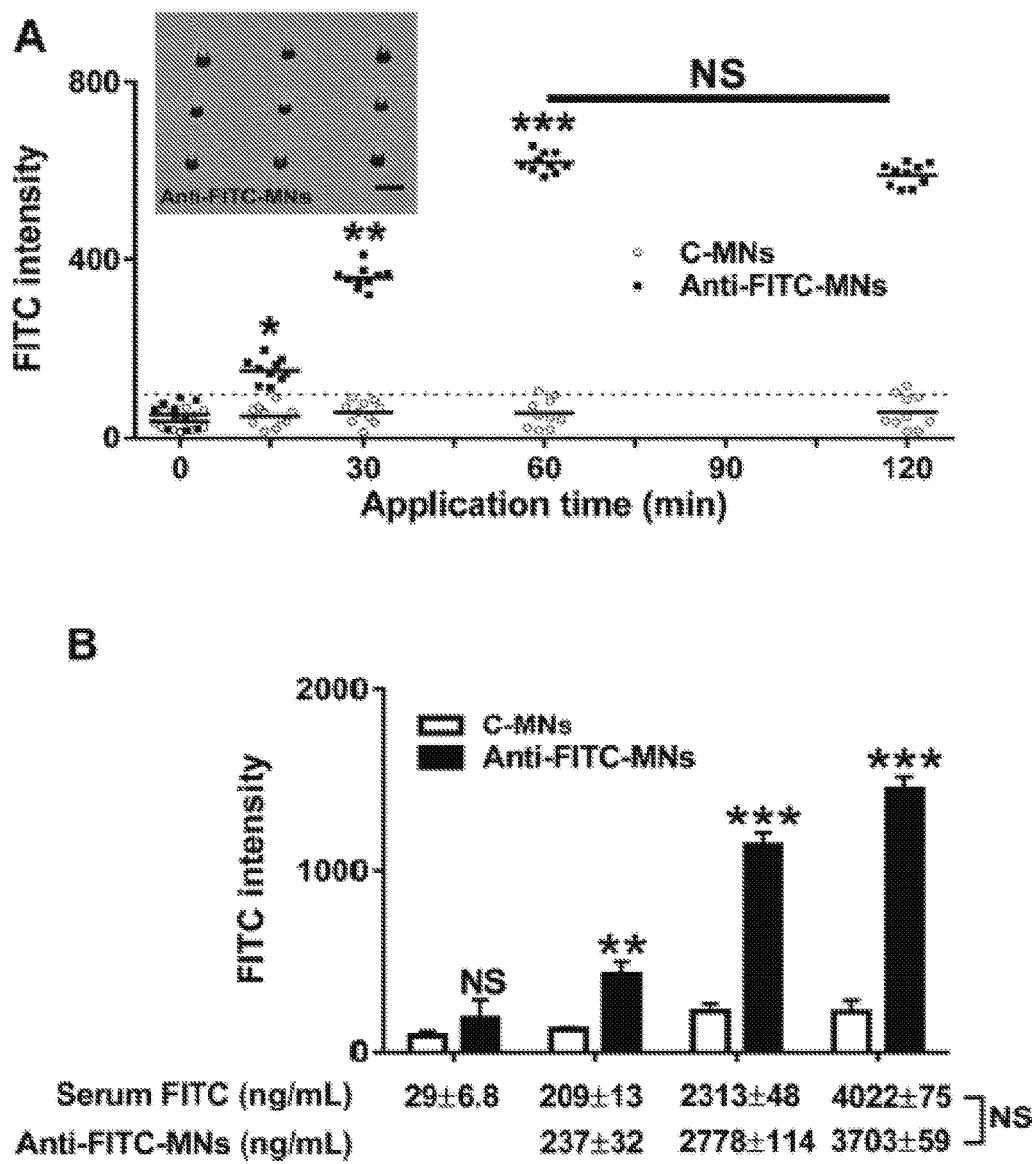
FIGS. 10A-B illustrate quantification of circulating FITC by anti-FITC-MNs in laser-treated skin.

The high level and even accumulation of circulating biomarkers in the skin after laser illumination should result in robust improvement of MNs-based assays. To test this, mice receiving 100 mL FITC at 4 mg/mL were treated with laser as above, followed by application of anti-FITC-MN or C-MN patch into laser-treated skin. The patches were removed at indicated times and FITC intensities were measured as FIG. 8D. As can be seen in FIG. 10A, only one or two C-MN arrays among 10 arrays tested demonstrated FITC signal barely reaching or above the cutoff level in one or 2 h assays. In comparison, FITC could be significantly detected by anti-FITC MNs as early as 15 min into the assay ($P<0.05$). Extending a duration to 30 min raised the level of FITC detection 3-fold greater than the cutoff value ($P<0.01$). An additional 2-fold increase in FITC capture on anti-FITC-MNs was achieved by prolonging the application time from 30 min to 1 h ($P<0.001$), and no further increment was attained by extending to 2 h from 1 h application (FIG. 10A). A markedly shortened time of detection, from 4-6 h to 30 min, confers great potentials for point-of-care diagnosis and onsite monitoring of biological states. Moreover, the lack of an increase in specific binding after prolonged insertion can minimize false positives from unintentionally extending insertions into the skin. In addition, the level of FITC captured on the array was 5-fold greater in the presence than in the absence of laser treatment, comparable to that obtained in standard immunofluorescence assays run in parallel. Most importantly, FITC captured on each array did not differ significantly among the ten arrays tested at different times (FIG. 10A), profoundly improving the reliability of the assay. The deviation was 13.57, which was in a range of conventional immunofluorescence assays (9.45). Meanwhile, experimental error in the absence of laser treatment was 88.21, 6.5 times higher and unacceptable for clinical diagnosis.

In marked contrast to the uneven signals appearing on anti-FITC-MNs in a similar array when inserted into non-laser-treated skin (FIG. 8D, inset), photographs indicated strong and uniform FITC signals presented on all anti-FITC-MNs in each array (FIG. 10A, inset). This uniform binding of FITC on each MN is a prerequisite to detecting multiple biomarkers in a single array, a technology that is long sought after in today's medicine. Furthermore, because the MNs reach only the upper dermis through the epidermis, the patch application should be painless as there are few nerves in the upper dermis or the epidermis. Thus, laser treatment of a tiny area of the skin safely and conveniently offers the following advantages: (1) greatly enhancing the sensitivity of MNs-based arrays as a result of vigorous accumulation of circulating biomarkers in the upper dermis; (2) substantially reducing the measurement error from one test to another, making the assay highly reliable for diagnosis; (3) allowing uniform capture on each MN in the same array and thus making it possible to accurately detect multiple biomarkers in a single patch; and (4) minimally invasive and painless.

To correlate fluorescence intensity on anti-FITC MNs to FITC concentrations in circulation, FITC at different concentrations was i.v. administered into the separate groups of mice, followed by insertion of C-MNs and anti-FITC-MNs into the different sites of laser illumination for 30 min as above; meanwhile, a small blood sample was taken from each mouse via its tail vein immediately after MN patch application. Plasma was prepared from the blood by centrifugation at 1000 g for 10 min, followed by filtering through a membrane with 10,000 MW cutoff. The resultant FITC concentrations in the ultrafiltrates were determined by fluorescence spectrophotometer, which is commonly used to measure FITC in serum samples. FITC concentrations in the blood were 29±6.8, 209±13, 2313±48, and 4022±75 ng/mL corresponding to i.v. injections of 100 mL FITC at 0.4, 4, 40, and 80 mg/mL, respectively. The amounts of FITC detected by anti-FITC-MNs were 237±32, 2778±114, and 3703±89 ng/mL for mice receiving 100 mL FITC at 4, 40, and 80 mg/mL, after normalization with a tissue dilution factor 3 mentioned above. Thus, FITC concentrations measured via serum samples and MNs yielded remarkably close results (FIG. 10B). The FITC level was undetectable by MNs in mice i.v. injected with 0.4 mg/mL of FITC (FIG. 10B).

Measurement of Anti-HA IgG in Immunized Mice

Figure 11:
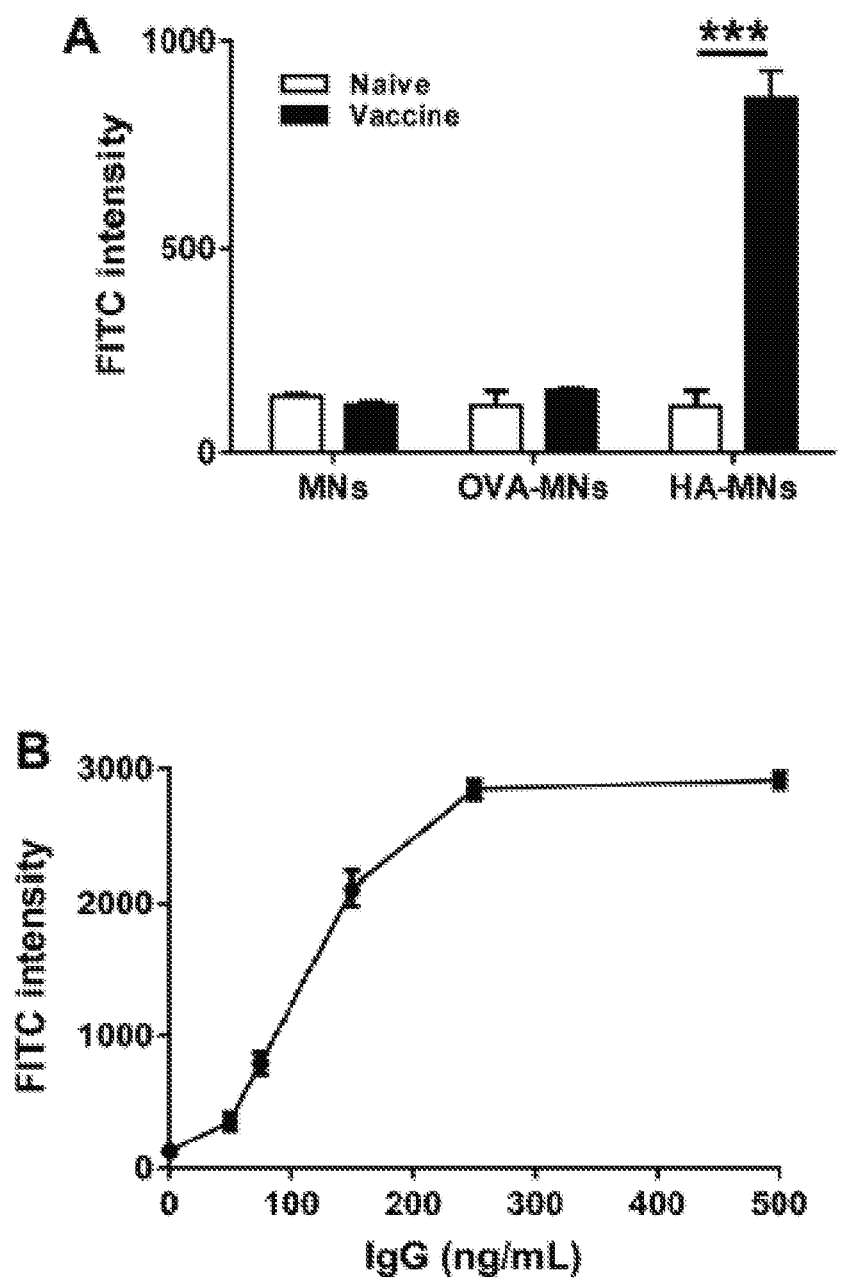
FIGS. 11A-D illustrate measurement of anti-HA IgG in immunized mice.
Figure 11:
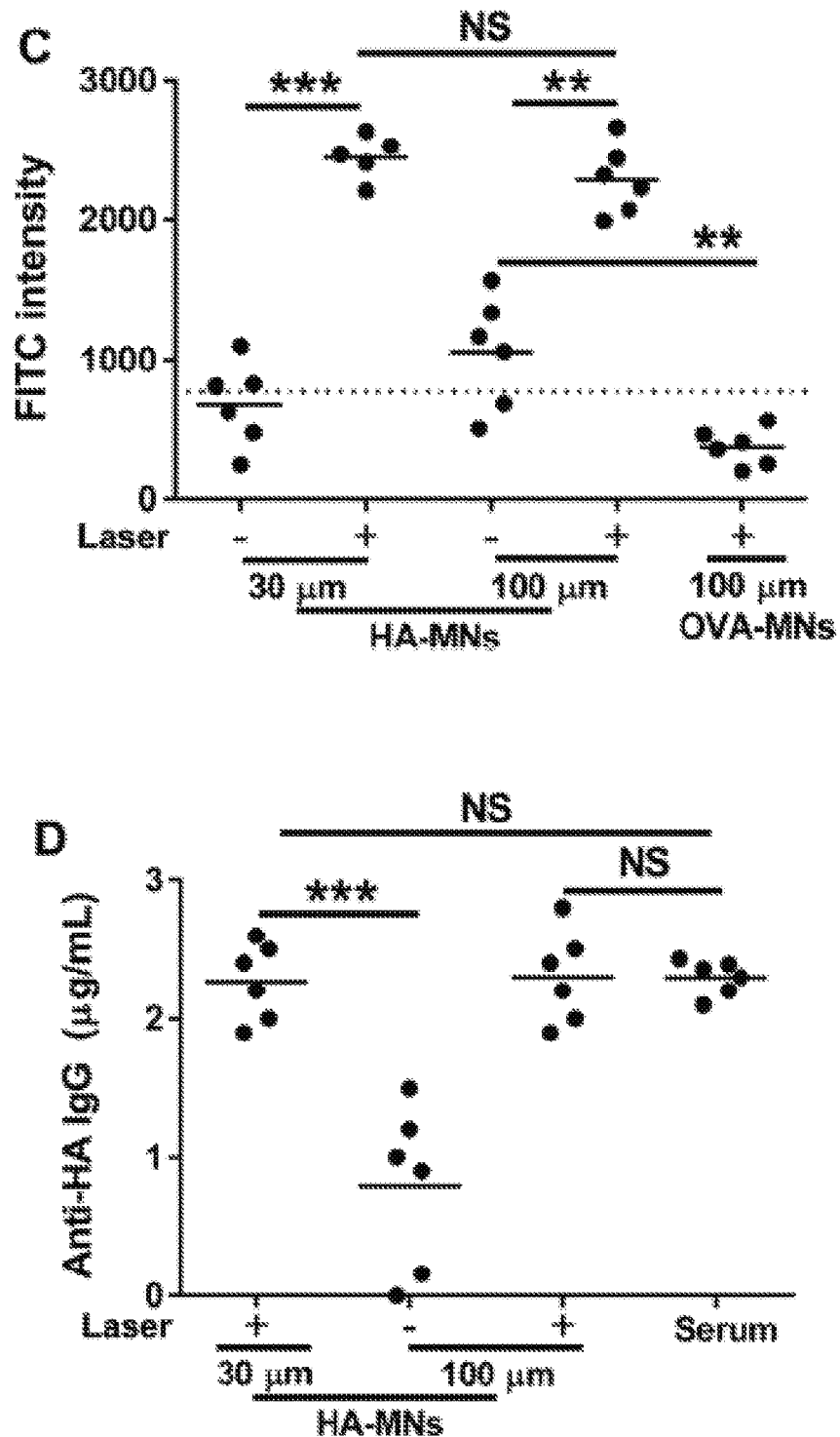

Small biomarkers differ from macromolecules in terms of leakage, diffusion, binding dynamics from dermal capillary to perivascular skin tissue, and FITC injected may also differ from natural biomarkers. We thus tested whether this novel approach could measure clinically relevant macromolecules as sufficiently as FITC. To this end, influenza hemagglutinin (HA) protein or control ovalbumin (OVA) was mounted on MNs to generate HA-MNs and OVAMNs arrays as described (Jin, J. et al., 2014; Muller, D A et al., 2012). The specificity and sensitivity of resultant MN arrays were verified by incubation of the array for 30 min with 1:300 diluted serum prepared from immunized mice or 1:100 from control mice, and then with FITC-conjugated secondary antibody (FIG. 11A). Strong fluorescence signal was seen only on HA-MNs incubated with serum of immunized mice, not naïve mice. No positive FITC binding was detected over background either on uncoated MNs or OVA-MN controls irrespective of the serum incubated with, confirming specific binding of anti-HA antibody on HA-MNs. Moreover, with known concentrations of anti-HA IgG, HA-MNs were confirmed to be able to measure anti-HA IgG at a concentration as low as 50 ng/mL in proportional correlation with anti-HA IgG concentrations in a range from 50 to 250 ng/mL (FIG. 11B).

HA-MNs and OVA-MNs of 30 mm and 100 mm in length were then employed to capture anti-HA IgG in the upper or deep dermis, respectively, in mice that received influenza vaccines 4 weeks prior. Out of 6 HA-MNs at 100 mm length, 4 could capture anti-HA IgG above the cutoff value from deep dermis after 30 min insertion ($P<0.05$), but the 30 mm HA-MNs did not capture anti-HA IgG above the cutoff level with statistical significance (FIG. 11C). As the dermis contains nerves and touch receptors, insertion of MNs into the dermis is expected to bring about significant pain. Moreover, longer MNs are relatively easier to break than shorter MNs upon insertion, which may cause unwanted adverse events. These adverse events were effectively circumvented with laser treatment that enabled 30 mm HA-MNs to capture anti-HA IgG at levels 4-time greater than the cutoff level in the upper dermis (FIG. 11C, $P<0.001$). Interestingly, there was no difference in specific antibody binding between 30 and 100 mm HA-MNs in the presence of laser illumination, confirming uniform distribution of anti-HA IgG throughout the dermis as shown in FIG. 9B. This is of highly clinical significance if the amount of IgG measured by the assay is independent on the depth of MNs or a longer time of the insertion. It can be envisioned that potential errors of the measurement would arise substantially when MN arrays are applied by different people at various places where time of insertion may not be well controlled and the force of insertion of the patch may vary from one person to the other. These errors would be eliminated effectively if laser pre-illumination is applied to the site of MNs application as demonstrated in this Example. In parallel, OVA-MNs were negative irrespective of the MN length or in the presence or absence of laser treatment (FIG. 11C and data not shown). The amount of anti-HA IgG measured on HA-MNs was 235±21 ng/mL based on the standard curve (FIG. 11B). The blood concentration would be ~11 times higher than this number after calibration by the factor of skin tissue dilution, which was estimated in the basis of Evans blue dilution in the skin mentioned above. The result was strikingly close to the 2.31±0.14 mg/mL obtained by a traditional IF assay of the sample run at the same time (FIG. 11D). Finally, the deviations of 30 and 100 mm HA-MNs with laser treatment were 0.21 and 0.33, respectively, which were similar to a traditional IF assay that was about 0.14 in parallel tests. In comparison with a deviation of 0.95 in MNs-based analysis alone, a greater than 4-fold precision increase was achieved by simple and brief laser irradiation.

Measurement of Anti-HA IgG in Immunized Swine

Figure 12:
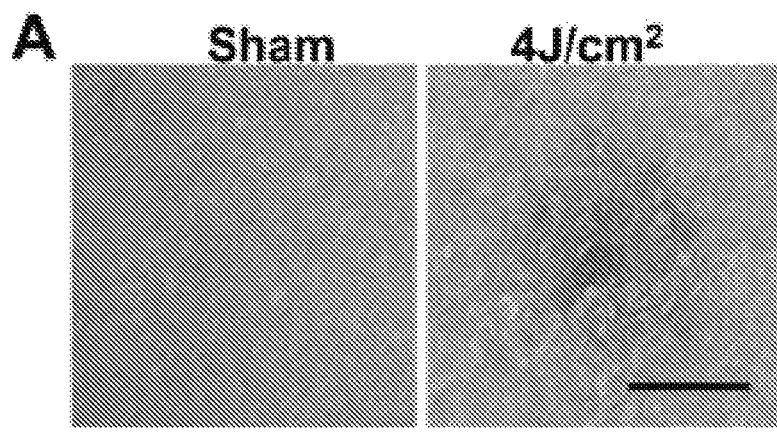
FIGS. 12A-D illustrate extravasation and skin reaction after treating swine with a long pulse 595 nm laser.
Figure 12:
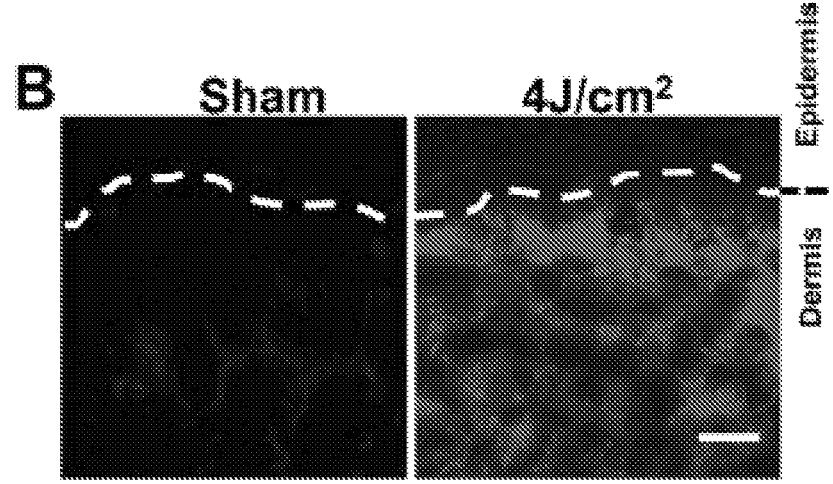
Figure 12:
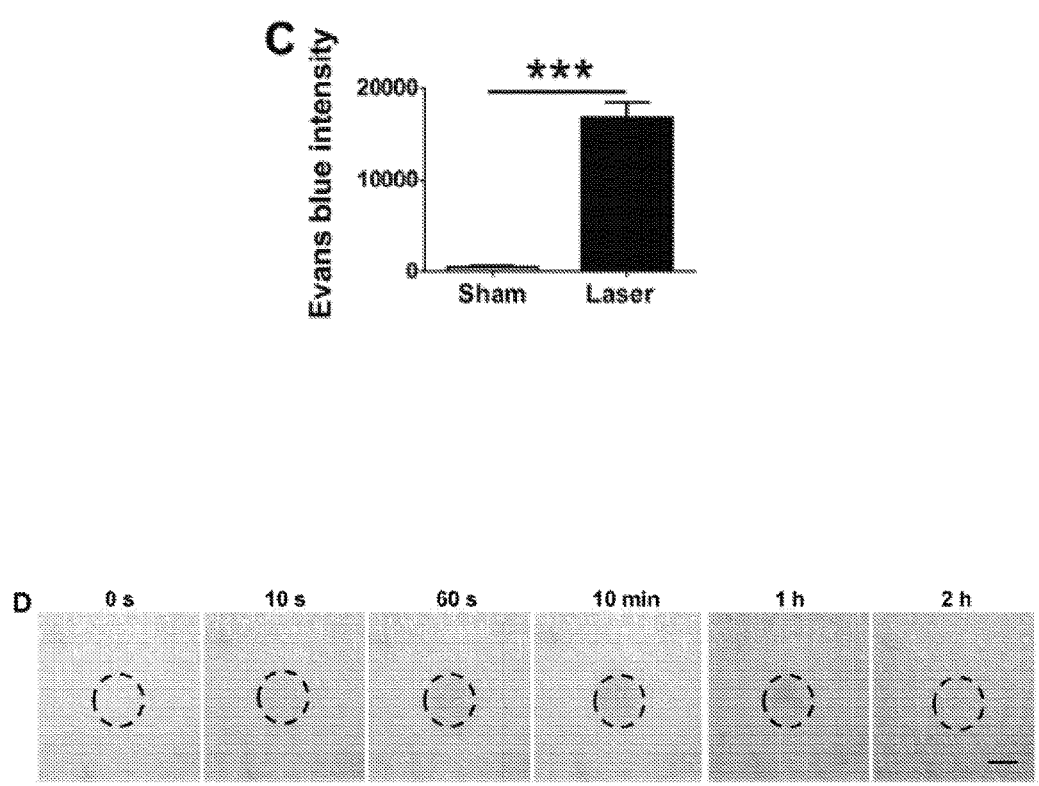

The skin of swine is anatomically and physiologically more similar to that of humans than mice. The assay was validated in pigs receiving influenza vaccines in order to determine its clinical potential. A clinical, long pulse 595 nm laser was used to illuminate the site of HA-MN array application because of its common use in humans. Prior to laser illumination, Evans blue dye at 20 mg/mL and 20 mL per pig was intravenously administered before different sites of the pig skin were illuminated with the laser at varying energy densities from 7 to 4 $J/cm^2$ to avoid rupturing any vessels, which is much lower than 7.5-20 $J/cm^2$ energy power used in the clinic. Ten minutes after laser illumination, a significant amount of Evans blue dye could be seen by naked eyes (FIG. 12A). To our surprise, Evans blue extravasation appeared not to arise with increasing density of laser energy but skin injury did. The lowest energy density of 4 $J/cm^2$ of the laser device was then chosen, which was a half of the lowest laser energy used in clinics. Similar to what was described in mice, the laser setting resulted in a strong and uniform distribution of Evans blue fluorescence in the upper dermis, contrasting that of skin from the same pigs un-treated by laser (FIG. 12B). The increment in fluorescence intensity in the upper dermis was about 1000-fold higher than controls (FIG. 12C). To determine the tissue dilution factor, Evans blue was extracted from the skin of 5×5 $mm^2$, 2 mm depth and the amount in laser-treated skin was about 5.7 mg/mL as determined by fluorescence spectrophotometer, which was 15.7 times lower than that in serum. The greater dilution factor compared to that in mice may be associated with the laser and size of the body or velocity of the blood in pigs. Skin redness was observed 1 min after the illumination, which peaked at 10 min, but subsided gradually thereafter and completely normalized within 2 h of laser illumination (FIG. 12D). Clinical description of pain levels with 7.5 $J/cm^2$ is about 1-2 and the pain induced by 4 $J/cm^2$ should be less than that.

Figure 13:
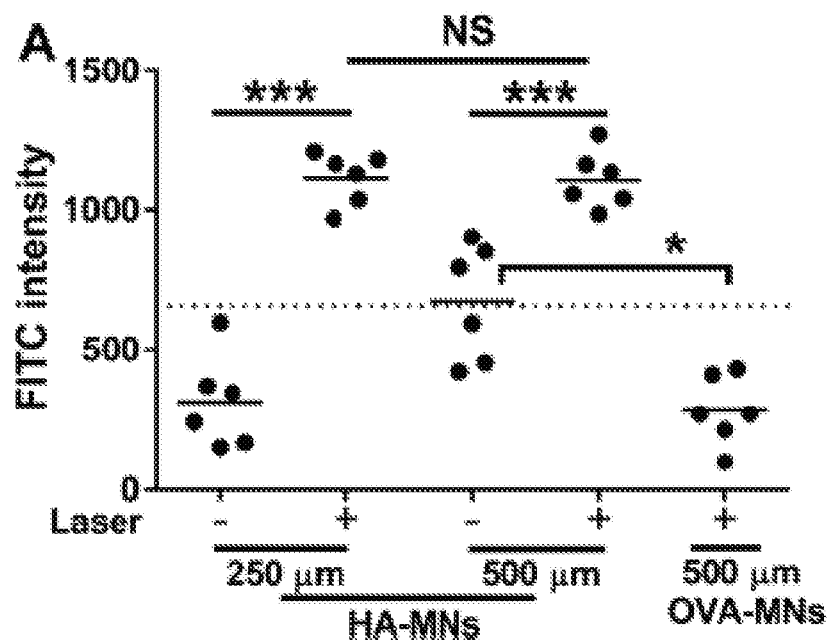
FIGS. 13A-B illustrate measurement of anti-HA IgG in immunized pigs.
Figure 13:
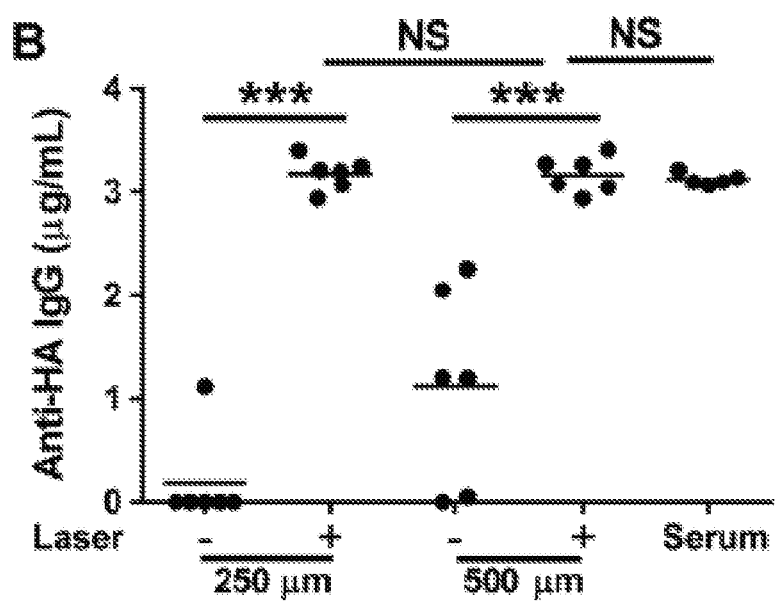

We fabricated 250 and 500 mm HA-MNs and OVA-MNs to accommodate the thicker skin of pigs and verified their specificity similarly as described in the mouse study (FIG. 11A). The HA-MNs penetrated either directly into upper dermis or dermis of pigs receiving influenza vaccines two weeks ago or into the site of laser illumination in the same pigs. In the absence of laser illumination, 250 mm HA-MNs failed to capture a significant amount of anti-HA IgG over background after 15 min application (FIG. 13A). Although 500 mm HA-MNs could detect anti-HA IgG above the cutoff level under a similar condition, the results were inconsistent among different arrays (FIG. 13A). In contrast, in the presence of laser illumination, anti-HA IgG was strongly and consistently detected by all HA-MNs at a length of either 250 or 500 mm for only 15 min application (FIG. 13B). The anti-HA IgG level was increased by more than 3-fold in the presence vs. the absence of laser illumination.

EXAMPLE 2

Immunization with radiation-attenuated sporozoites (RAS) via mosquito bites to induce sterile immunity against malaria in humans is neither practical nor ethical. In this Example, the inventor surprisingly found that intradermal (ID) inoculation of RAS into laser-illuminated skin confers immune protection against malarial infection almost as effectively as IV immunization. Brief illumination of the inoculation site with a low power 532 nm Nd:YAG laser enhanced the permeability of the capillary beneath the skin, owing to hemoglobin-specific absorbance of the light. The increased blood vessel permeability appeared to facilitate an association of RAS with blood vessel walls, ultimately promoting a 7-fold increase in RAS entering circulation and reaching the liver over ID administration. Accordingly, ID immunization of RAS at a laser-treated site stimulated much stronger sporozoite-specific antibody and CD8+IFN-γ+ T cell responses than ID vaccination and provided nearly full protection against malarial infection, whereas ID immunization alone was ineffective.

Materials and Methods
Animals and Parasites

Female BALB/c mice at 8 weeks of age were purchased from Charles River Laboratory. Mosquitoes carrying *Plasmodium yoelii*-GFP (PyGFP) sporozoites were provided by Insectary Core Facility of Langone Medical Center, New York University. Fresh fluorescent sporozoites were isolated by dissecting mosquitoes under stereomicroscopy. Purified, irradiated or non-irradiated *P. yoelii* sporozoites were preserved in the vapor phase of liquid nitrogen and provided by Sanaria (Maryland, USA).

Selective Blood Vessel Injury by Lasers

A 532 nm Nd:YAG laser (Spectra-Physics Inc., Mountain View, Calif.) and a 595 nm pulsed dye laser (Vbeam, Candela, Mass.) were used in this Example. To test the effects of lasers on the permeability of capillaries beneath the skin, FITC-conjugated dextran (MW 200,000) was injected into the tail vein to label blood vessels of mice, and the dorsal skin was then illuminated by lasers at different settings (Table 1).

TABLE 1

Parameters used in Example 2.

| Conditions | Wavelength | Pulse width | Diameter | Fluence | Energy |
|---|---|---|---|---|---|
| 1 | 532 nm | 5-7 ns | 7 mm | 1 J/cm$^2$ | 0.38 J |
| 2 | 532 nm | 5-7 ns | 7 mm | 9 J/cm$^2$ | 3.46 J |
| 3 | 595 nm | 0.45 ms | 7 mm | 5 J/cm$^2$ | 1.92 J |
| 4 | 595 nm | 0.45 ms | 7 mm | 20 J/cm$^2$ | 7.69 J |

Leakage of FITC-dextran in laser-treated skin was examined by intravital confocal microscopy (Olympus). Alternatively, the skin was treated with laser, followed by FITC-dextran injection and microscopic analysis to determine duration of the leakage. For histological examination, laser-treated skin was collected immediately after laser treatment, fixed in 10% formalin, and processed by standard hematoxylin and eosin (H&E) staining. Slides were analyzed by Nanozoomer Slide Scanner (Hamamatsu).

Confocal Microscopy of ID-injected Sporozoites

Texas red-conjugated dextran (MW 70,000) was injected intravenously to label blood vessels. *P. yoelii* sporozoites were stained with carboxyfluorescein succinimidyl ester (CFSE) for 5 min, washed twice by PBS, and resuspended in PBS. The stained sporozoites at a concentration of 5,000 sporozoites in 0.5 µl PBS were administered into mouse ears after illumination with 532 nm laser or sham light by a microliter syringe (Hamilton 1701 N). The ears were harvested 15 min after the injection, fixed in 10% formalin, and examined under a confocal microscope (Olympus).

Quantification of Parasite Loads in the Liver

To quantify parasite loads in the liver, mice were IV administered with varying numbers of sporozoites, and the liver was harvested 42 h later. Total RNA was extracted from an aliquot of the liver cells. Parasite-specific 18S rRNA was reverse transcribed and amplified by real-time PCR (the Roche SYBRGreen system) or RT-qPCR with primers: forward, 5'-GGGGATTGGTTTTGACGTTTTTGCG-3' (SEQ ID NO:1) and reverse, 5'-AAGCATTAAATAAAGC-GAATACATCCTTAT-3' (SEQ ID NO:2) (Hermsen, C C et al., *Mol. Biochem. Parasitol.* 118:247-251, 2001; Bruna-Romera, O et al., *Int. J. Parasitol.* 31:1499-1502, 2001). The housekeeping gene β-actin was used as an internal control using primers: forward, 5'-CTGGGACGACATGGA-GAAGATC-3' (SEQ ID NO:3) and reverse, 5'-GTCT-CAAACATGATCTGGGTCATC-3' (SEQ ID NO:4). The effect of laser on parasite loads in the liver was assessed by equivalency to the number of parasites in the liver after varying numbers of RAS were IV injected. For PyGFP sporozoites, equal amounts of freshly isolated PyGFP sporozoites were administered via IV or ID at laser-treated or sham-treated sites. Livers were harvested 42 h later and dissociated to prepare single cell suspension by a 70 µm cell strainer. Aliquots of liver cells were either extracted to obtain total RNA or analyzed by flow cytometry to count GFP+ cells in the liver.

Immunization and Challenge

Irradiated 2,000 *P. yoelii* sporozoites were either IV injected into the tail vein or ID injected into laser-treated or untreated dorsal skin. The immunization was repeated twice with 2-week intervals. Mice were challenged by IV injection of 200 non-irradiated *P. yoelii* sporozoites 7 days after the last immunization. Blood samples were collected for thin blood smears analyzing percent parasitemia from days 3 to 21 post-challenge after Giemsa staining under a Zeiss Axiophot microscope.

Immunofluorescence Assay of Sporozoite-specific Antibody

Sporozoite-specific antibody titer was measured by immunofluorescence assay 7 days after the final immunization as described (Epstein, J E et al., *Science* 334:475-480, 2011). Briefly, 2,000 sporozoites in 20 µl PBS containing 2% bovine serum albumin (BSA) were coated to each well of Cel-Line slides (Thermo Scientific) and air dried. Pre-immune sera were diluted at 1:50, while immune sera were serially diluted starting from 1:50. The slide was incubated with 20 µl diluted pre-immune and immune sera at 37° C. for 1 h in a moisture box. After washing three times in PBS, slides were incubated with FITC-conjugated rabbit anti-mouse IgG antibody for 1 h. After wash, vectashield mounting medium (Vector laboratories) was added to each well before placing a cover glass to the slide. The slides were examined under an Olympus BX51 fluorescence microscope at 400× magnification. Fluorescence intensity in each well was recorded and measured by ImageJ. The endpoint titer was defined as the highest dilution of immunized sera that had higher fluorescence intensity than the pre-immune sera.

Measurement of Sporozoite-specific T Cell Response

Mice were immunized three times each with 10,000 sporozoites administered by IV or ID in the presence or absence of laser illumination as detailed above. The mice were sacrificed 7 days after the final immunization and the liver, spleen, and blood were collected. The liver and spleen were dissociated by a 70 µm cell strainer. The cell suspensions, along with blood samples, were treated with Ammonium-Chloride-Potassium lysing buffer to remove red blood cells, and lymphocytes were isolated using Percoll (33%) as described (Doll, K L et al., *Methods Mol. Biol.* 923:493-504, 2013). Lymphocytes were then stimulated with 1 mg/ml PyCSP 280-288 peptide (SYVPSAEQI) (SEQ ID NO:5) for 21 h at 37° C. with 1 µg/ml Golgin-plug in the culture for the final 5 h. The stimulated cells were harvested, fixed with 2% formaldehyde, permeabilized with permeabilization buffer (eBioscience), and stained with indicated antibodies. Among the antibodies used, PerCP-Cy5.5 anti-Mouse CD8α antibody (clone 53-6.7) was purchased from eBioscience; PE anti-mouse CD11a Antibody (M17/4), Alexa 647 antimouse CD90.2 (30-H12) antibody, and FITC anti-mouse IFN-γ antibody (XMG1.2) from Biolegend; and anti-mouse CD16/CD32 antibody (2.4G2) from BD Biosciences. The stained cells were assessed on FACSAria (BD Biosciences) and analyzed by FlowJo software (version 7.6.5).

Statistics

One-way ANOVA followed by Tukey's multiple comparison tests was used to analyze the differences among multiple groups. Two-way ANOVA followed by Bonferroni post tests was used to analyze the parasitemia and compare the differences among selected groups. Logrank test was used to analyze the survival data. All statistical analyses were performed using Prism GraphPad 6.

Results

Laser Illumination Alters the Permeability of Capillaries in the Skin

Figure 15:
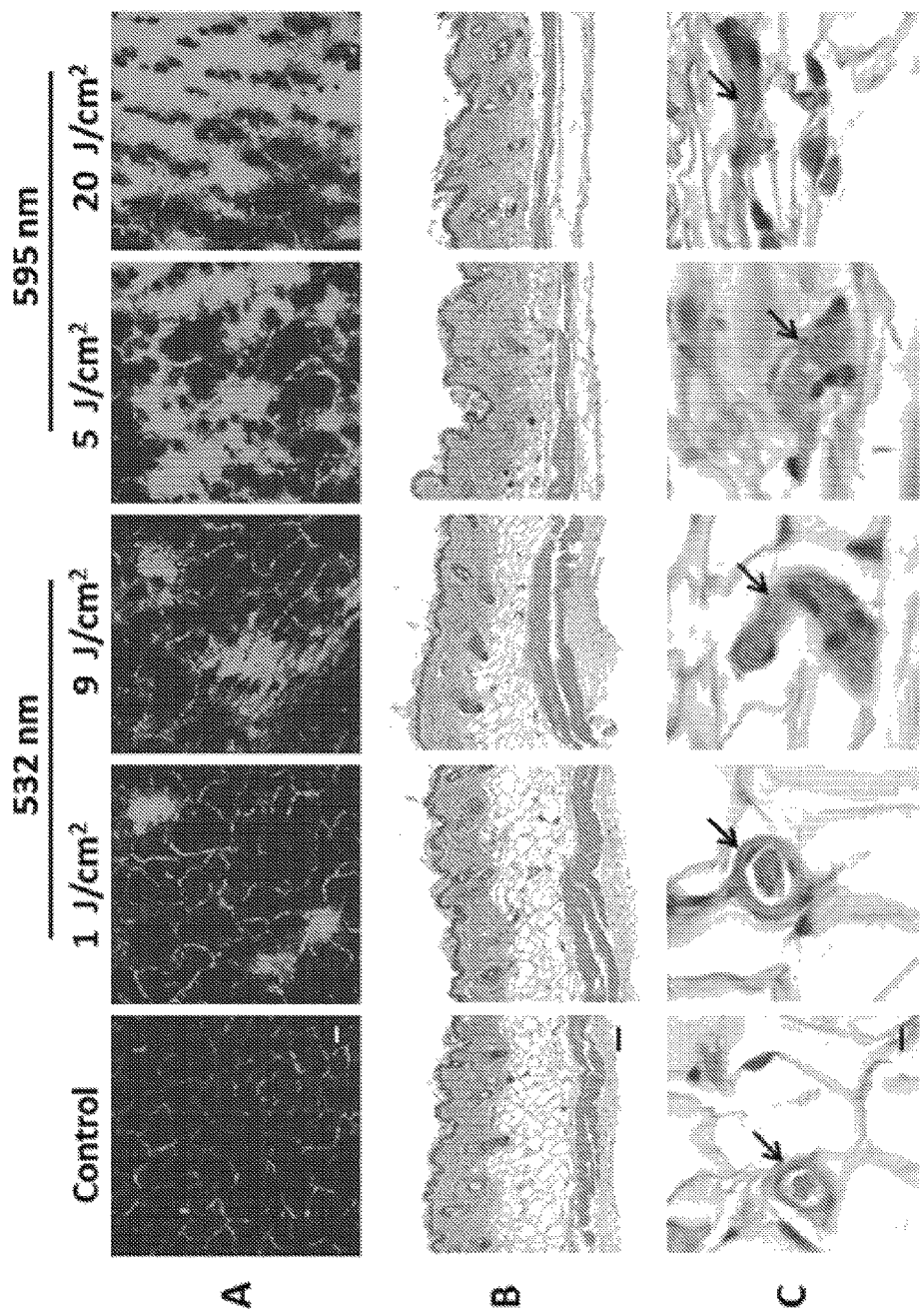
FIGS. 15A-C illustrate laser illumination enhances blood vessel permeability.

To mimic mosquito bites, laser was used to target blood vessels in the skin. Mice were IV injected with vessel-impermeable FITC-dextran to label the capillary network (FIG. 15A). After 532 nm laser treatment at a low dose of 1 J/cm$^2$, some dye leaked out and scattered over the laser-treated skin. Capillary vessels appeared to enlarge slightly compared with those in untreated skin (FIG. 15A, column 1 vs. 2). Slight enlargement of capillary vessels was corroborated by histological examination and notably, there was no leakage of red blood cells out of the vessel in spite of the enlargement (FIG. 15C, arrow). The surrounding tissue of the dilated vessel was also normal (FIGS. 15B-C). As expected, the 532 nm laser at a higher dose of 9 J/cm$^2$ (total energy of 3.46 J) led to more FITC-dextran leakage, concomitant with vessel injuries or rupture, as evidenced by leakages of red blood cells from the vessel (FIG. 15C). Treatment with the 595 nm laser at 5 J/cm$^2$ or 20 J/cm$^2$ resulted in robust leakage of FITC-dextran (FIG. 15A) or vessel rupture, respectively (FIG. 15C).

Laser Promotes Delivery of ID-injected Sporozoites to the Liver

Figure 16:
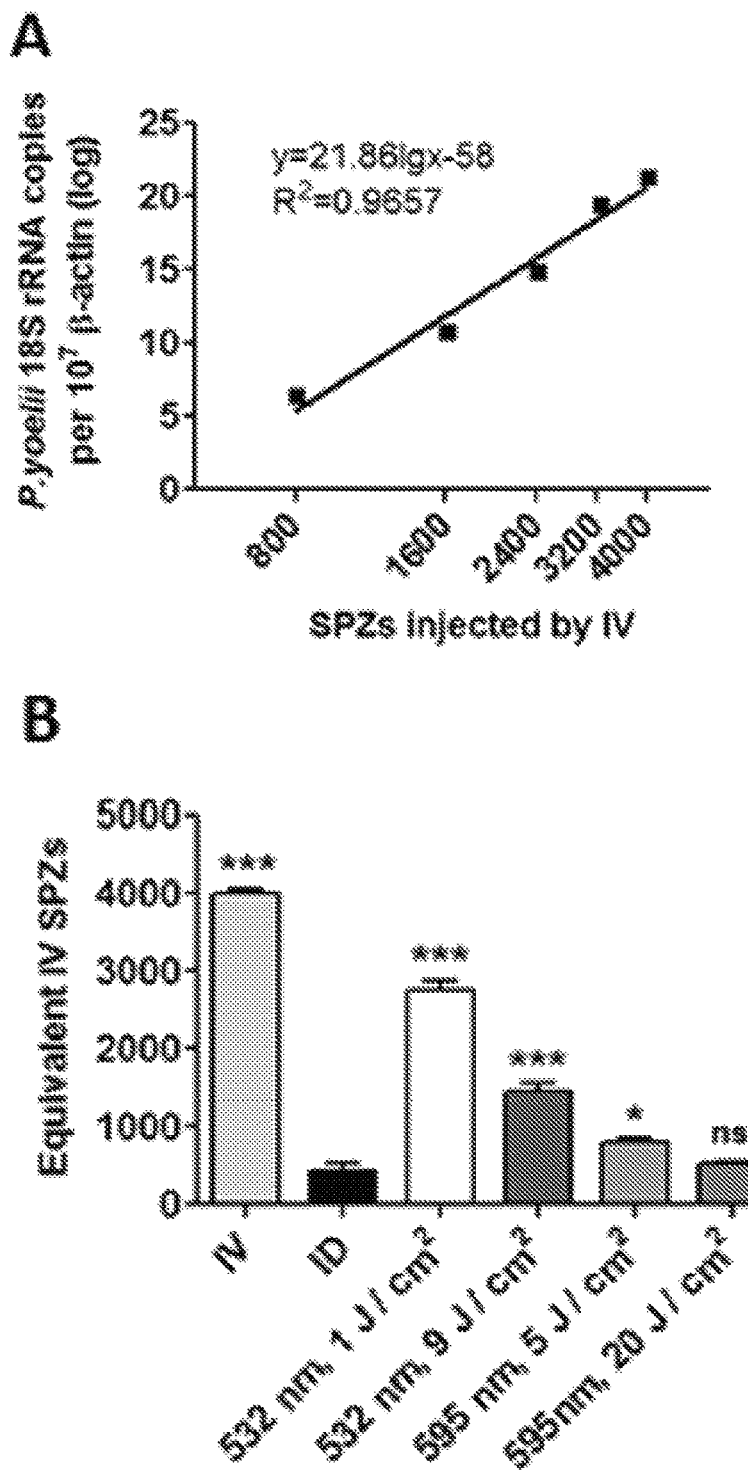
FIGS. 16A-D illustrate that laser enhances the delivery of sporozoites from the skin to liver.
Figure 16:
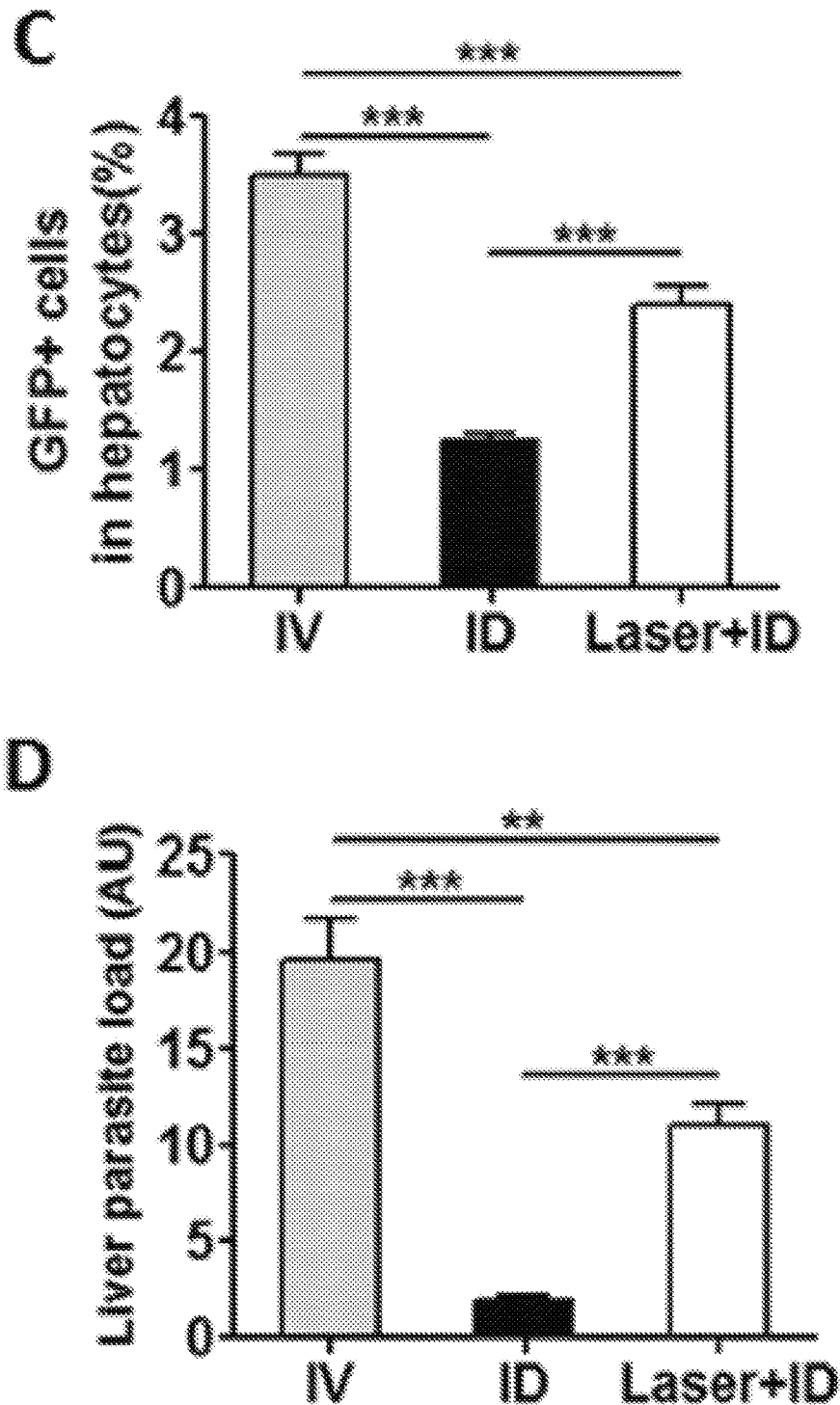

Whether the laser could promote delivery of ID injected sporozoites to the liver was then investigated. Since RAS did not replicate in the liver and could not be detected by RT-qPCR (data not shown), non-irradiated sporozoites were used instead. The amount of sporozoites that reached the liver after ID injection was calculated based on a standard curve generated by IV injection of varying numbers of sporozoites (FIG. 16A). As shown in FIG. 16B, ID injection of 4,000 sporozoites resulted in a parasite load that was equal to IV injection of about 400 sporozoites, suggesting that only 10% sporozoites entered blood circulation after ID inoculation. In contrast, illumination of the skin with 532 nm laser at 1 J/cm$^2$ gave rise to parasite liver loads equivalent to IV injection of about 2,800 sporozoites (FIG. 16B), indicative of a 7-fold increase over ID inoculation alone. Surprisingly, a high dose of laser at 9 J/cm$^2$ enhanced liver-delivery of sporozoites by only 4-fold. The less efficiency of laser at a higher dose hinted that severe blood vessel damage might reduce skin-to-liver delivery of sporozoites. Continuous flow of the bloodstream at the inoculation site might be crucial for sporozoites trafficking to the liver. Too much capillary damage by 595 nm laser may adversely affect traveling of sporozoites from the skin to the liver. Another possibility was that coagulation of red blood cells inhibited the motility of sporozoites. Consistent with this, the 595 nm laser did not enhance sporozoite delivery to the liver as effectively as 532 nm laser. Illumination with 595 nm laser for 5 J/cm$^2$ only increased the delivery by 2-fold and no significant increase was seen with 20 J/cm$^2$. Accordingly, the 532 nm laser at 1 J/cm$^2$ was used in subsequent studies.

We next corroborated the effects of laser skin treatment on the trafficking of freshly isolated PyGFP sporozoites after ID administration, since cryopreserved sporozoites used in the preceding experiment might have low vitality and infectivity. As shown in FIG. 16C, the percentage of GFP+ cells in the liver was significantly higher in the presence of laser treatment than in the absence of the treatment. Liver parasite loads were also much higher in Laser+ID group than in ID group (FIG. 16D). These results suggest that laser could enhance skin-to-liver delivery of sporozoites whether the sporozoites are freshly isolated or cryopreserved.

Figure 17:
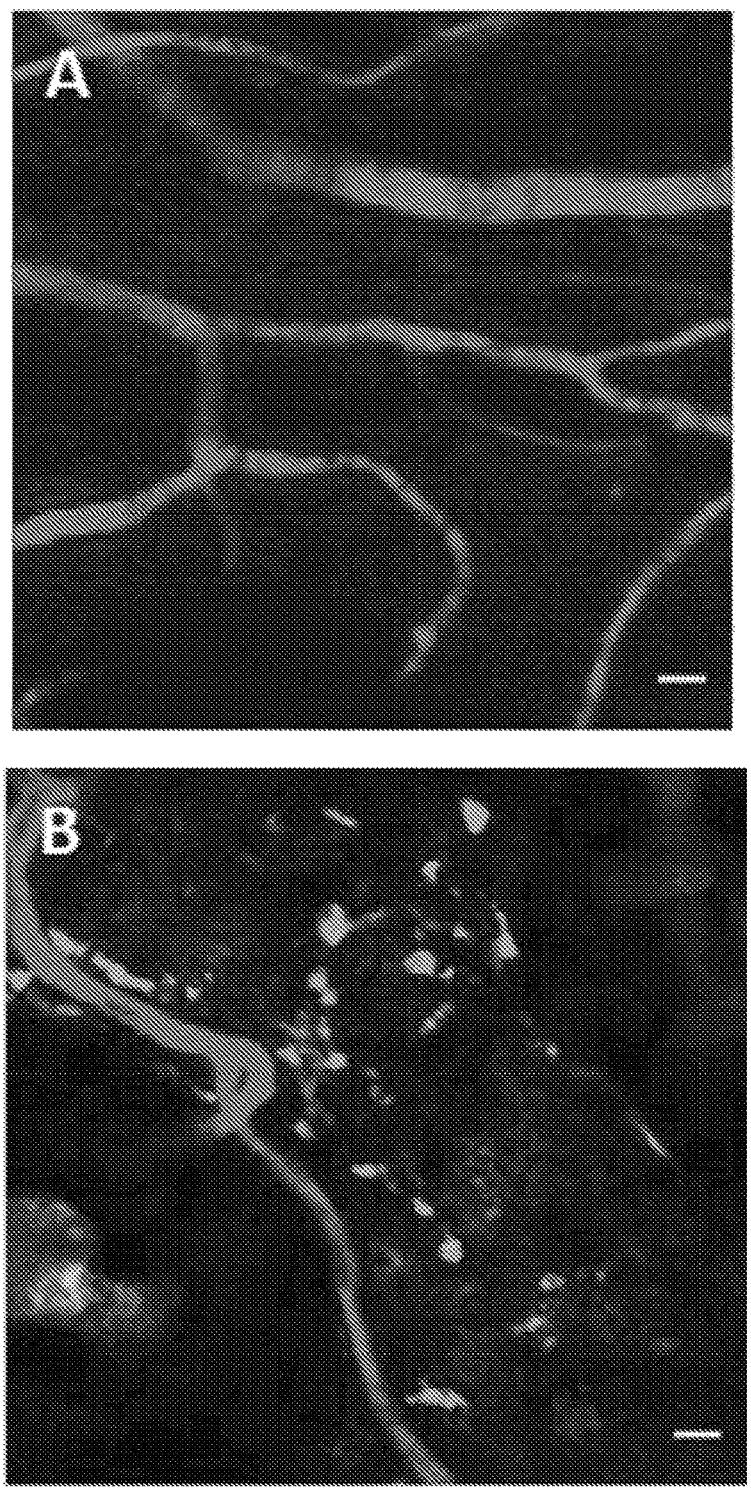
FIGS. 17A-D illustrate confocal microscopy of sporozoites in the skin.
Figure 17:
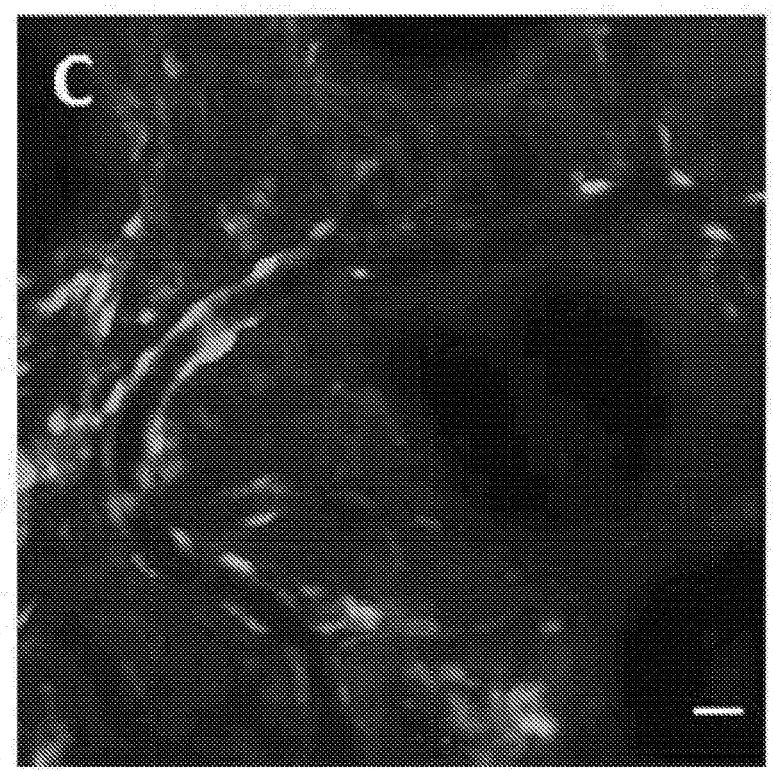
Figure 17:
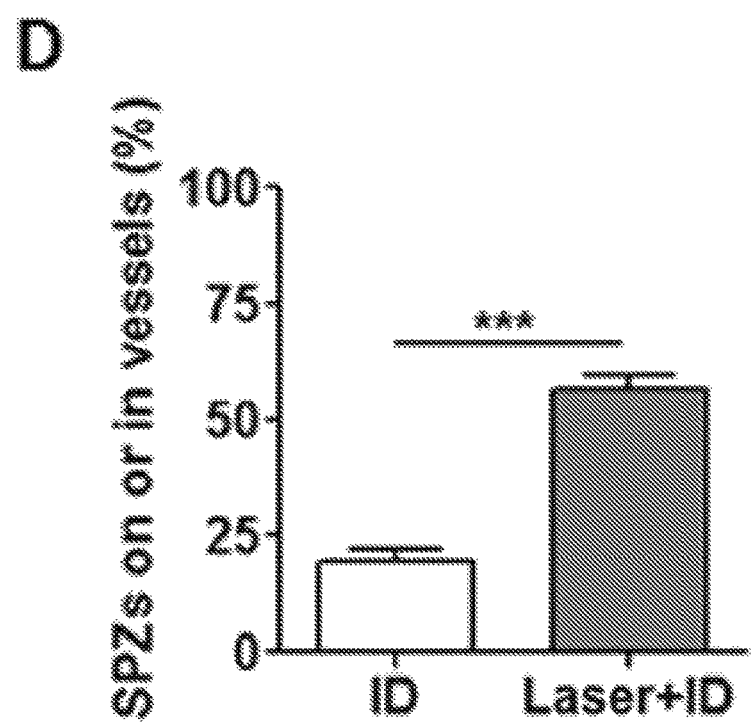

To determine how laser treatment of the skin could facilitate delivery of ID-injected sporozoites to the liver, sporozoites were fluorescently labeled and injected into laser-treated or untreated skin, followed by confocal microscopic analysis. After ID injection, most sporozoites were randomly scattered in the skin, and only a few sporozoites were close to blood vessel walls in the absence of laser treatment (FIG. 17B). In contrast, many sporozoites bound tightly to blood vessel walls and some entered the vessels in laser-treated skin (FIG. 17C). The percentage of sporozoites that were associated with or inside blood vessels was significantly higher in Laser+ID group than in ID group (FIG. 17D). The observations suggest that laser treatment of the skin facilitated sporozoites moving toward and binding to blood vessels. Increased association of sporozoites with blood vessels was consistent with their efficient entrance into the bloodstream.

Laser Enhances the Immune Responses Provoked by ID Immunization of Sporozoites

Figure 18:
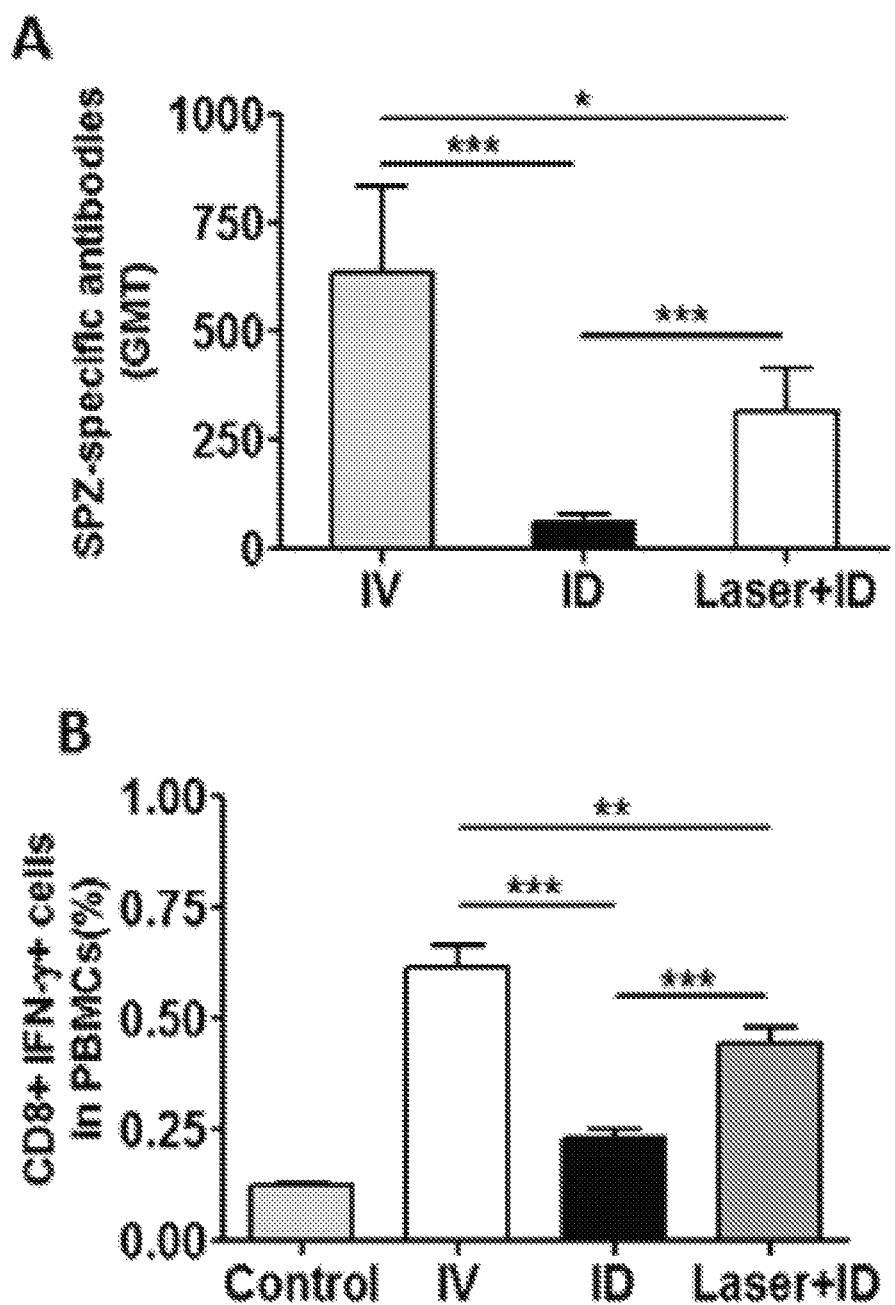
FIGS. 18A-B illustrate peripheral immune responses against sporozoites. Mice were immunized with three doses of RAS each with 10,000 sporozoites at an interval of two weeks. Geometric mean titers (GMT) of anti-sporozoite antibody were determined by immunofluorescence assay (FIG. 18A) and CD8+ T cells in PBMCs were analyzed by flow cytometry (FIG. 18B) 7 days after the final immunization. The results are expressed as means±SD (n=8, $*p<0.05$, $p<0.01$, and $*p<0.001$)

Laser-mediated enhancement in delivery of ID-injected sporozoites to the liver should translate into stronger immune responses. To verify this, the lower dorsal skin of mice was illuminated by laser, followed by ID inoculation of 10,000 RAS, while control mice received either IV or ID injection of an equal amount of RAS. After three immunizations, sporozoite-specific antibody titer was measured by immunofluorescence assays. As shown in FIG. 18A, anti-sporozoite antibody titer was substantially higher in laser+ID group than in the ID group, although it was lower than that in the IV group. Likewise, CD8+IFN-γ+ T cells in peripheral blood mononuclear cells (PBMCs) in Laser+ID group were significantly higher than those in ID group. The level of CD8+IFN-γ+ T cells was comparable to that in IV group (FIG. 18B).

Figure 19:
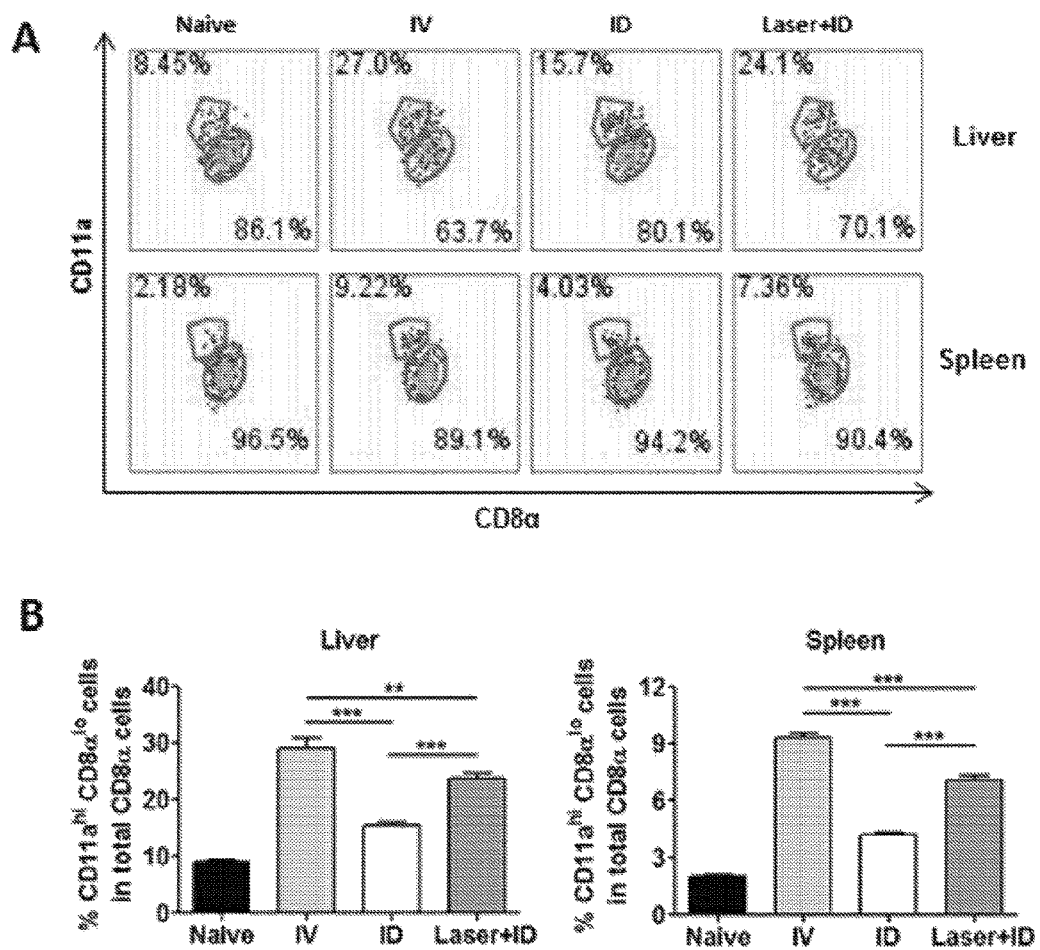
FIGS. 19A-C illustrate frequencies of sporozoite-specific CD8+ T cells in the liver and spleen. Mice were immunized with three doses of RAS each with 10,000 sporozoites at an interval of two weeks. Representative flow profiles of sporozoite-experienced $CD11a^{hi}$ $CD8\alpha^{lo}$ cells in the liver and spleen are shown in FIG. 19A. Mean frequencies ±SD of $CD11a^{hi}$ $CD8\alpha^{lo}$ cells (FIG. 19B) and IFN-γ+− producing CD8+ T cells (FIG. 19C) were attained in the liver and spleen by flow cytometry 7 days after the final immunization (n=8, $p<0.01$, $*p<0.001$ and ns, not significant)
Figure 19:
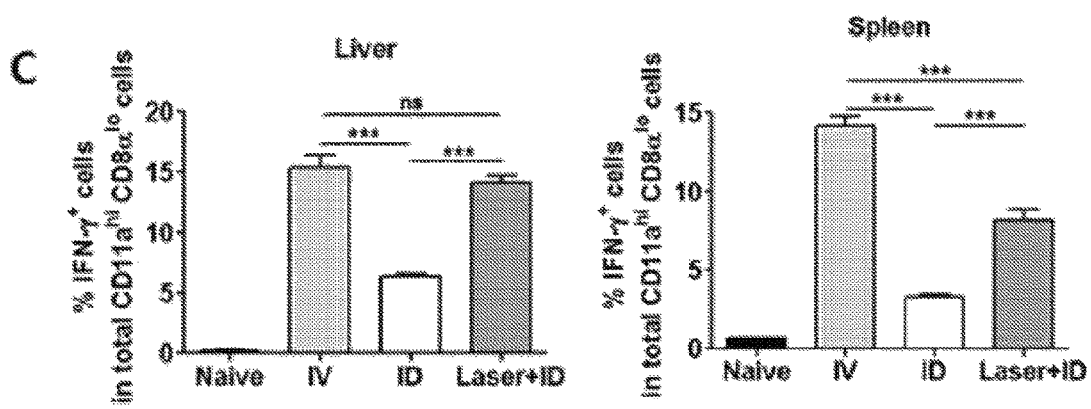

It has been reported that protection against malarial infection depends on sporozoite-specific CD8+ T cells producing IFN-γ in the liver. When naive CD8+ T cells encountered sporozoites, the cells expressed a reduced level of CD8α while increasing CD11a on the cell surface. Thus, percentages of CD11a$^{hi}$ CD8α$^{lo}$ cells were analyzed in the liver and spleen, and these cells were found to be significantly higher in the presence of laser treatment than in the absence of the treatment (FIGS. 19A-B). Moreover, upon stimulation with a sporozoite T cell epitope peptide derived from the circumsporozoite protein (SEQ ID NO:5), significantly higher percentages of cells secreting IFN-γ were attained in Laser+ID group than in the ID group and in both the liver and spleen, confirming that Laser+ID immunization induced stronger immune responses than ID immunization alone (FIG. 19C).

Laser Plus ID Immunization Offers a High Level of Protection Against Malarial Challenge A challenge study was next carried out to determine the efficacy of laser plus ID vaccination. Mice were immunized three times each with 2,000 RAS and challenged by IV injection of 200 infectious sporozoites 7 days after the last immunization. Blood parasitemia revealed that 7 out of 8 mice in Laser+ID group were protected, whereas all animals in ID group were infected (Table 2).

TABLE 2

Results of the challenge study.

| Immunization Route | Infected/injected | Protection |
|---|---|---|
| Un-immunized | 8/8 | 0 |
| IV | 0/8 | 100% |
| ID | 8/8 | 0 |
| Laser + ID | 1/8 | 87.5%*** |

***p < 0.001 compared with ID group

Figure 20:
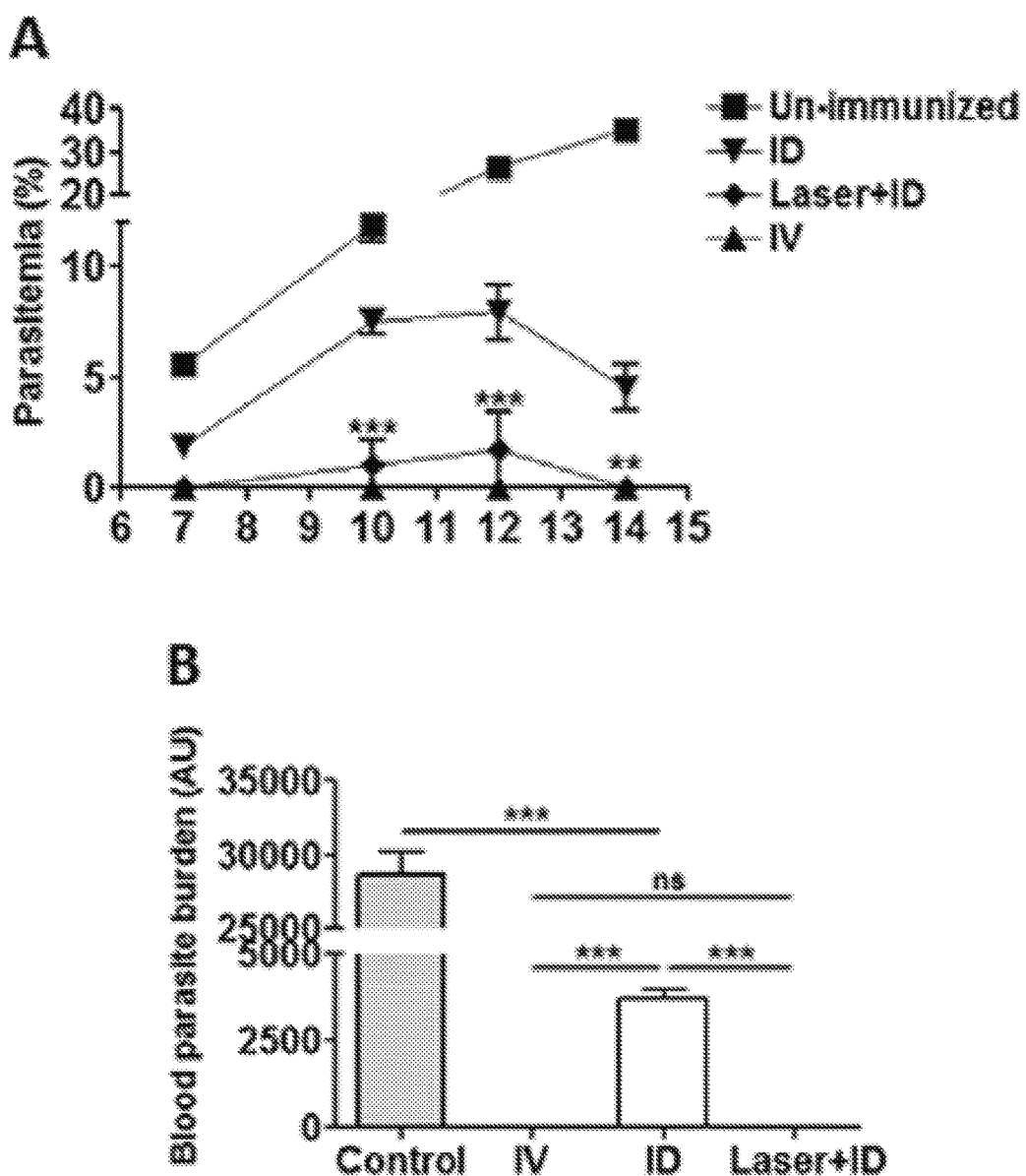
FIGS. 20A-B illustrate protection against malarial challenge. Mice were immunized with three doses of RAS each with 2,000 sporozoites at an interval of two weeks. All animals were challenged by IV injection of 200 live *P. yoelii* sporozoites 7 days after the final immunization. Parasitemias were monitored at indicated days post-challenge by blood smear (FIG. 20A) and blood parasite burdens were determined by RT-qPCR on day 10 post-challenge (FIG. 20B). The results are expressed as mean±SD (n=8, $p<0.01$ and $*p<0.001$ between ID and Laser+ID group in FIG. 20A or $***p$, 0.001 and ns, not significant in FIG. 20B).

The protection rate of Laser+ID group was 87.5%, which was comparable to that of IV group, and significantly higher than the ID group (p<0.001). Percent parasitemia in Laser+ID group was significantly lower than that of ID group (FIG. 20A). This result was also verified by RT-qPCR analysis of blood parasite loads (FIG. 20B).

From the above description, those skilled in the art will perceive improvements, changes and modifications. For example, the methods 34, 42, 46, and 50 are illustrated as process flow diagrams with flowchart illustrations. For purposes of simplicity, the methods 34, 42, 46, and 50 are shown and described as being executed serially; however, it is to be understood and appreciated that the present disclosure is not limited by the illustrated order as some steps could occur in different orders and/or concurrently with other steps shown and described herein. Such improvements, changes and modifications are within the skill of one in the art and are intended to be covered by the appended claims. All patents, patent applications, and publication cited herein are incorporated by reference in their entirety.

What is claimed is:

1. A device comprising:
   at least one penetration member having a body defined by oppositely disposed proximal and distal ends, the body having a length such that at least a portion of the distal end extends into a dermis of the skin of a subject when the device is contacted with the subject's skin; and
   a laser source coupled to the at least one penetration member so that, upon activation, the laser source is configured to deliver a laser beam into the dermis for a time sufficient to induce leakage or rupture of at least one blood vessel comprising the dermis;
   wherein at least a portion of the distal end is coated with one or more detection reagents for detecting one or more target analytes in the fluid leaked from the at least one blood vessel.

2. The device of claim 1, wherein the penetration member is a needle, a microneedle, or a microprojection comprising a microneedle array or a microprojection array.

3. The device of claim 1, wherein the penetration member is hollow and the laser source is coupled to an optical fiber that is at least partly disposed within the hollow penetration member.

4. The device of claim 1, wherein the penetration member is made of a solid, transparent material such that the laser beam is configured to penetrate into the dermis via the penetration member.

5. The device of claim 1, wherein at least part of the device is configured as a handheld, point-of-care device.

6. The device of claim 1, wherein the laser source is configured to deliver a laser beam having a wavelength that excites at least one of hemoglobin and oxyhemoglobin present in the at least one blood vessel.

7. The device of claim 1, further including a data component comprising:
   a memory storing computer-executable instructions; and
   a processor to access the memory and execute the computer-executable instructions to at least:
      record data generated upon detection of the target analyte;
      analyze the data; and
      display the data on a graphical user interface.

8. A method for collecting a fluid sample from the dermis of a subject, the method comprising the steps of:
   contacting a device with the skin of a subject so that at least a distal end of one or more penetrating members comprising the device directly contacts the dermis;
   activating a laser source coupled to the device to deliver a laser beam to the dermis for a time sufficient to induce leakage or rupture of at least one blood vessel comprising the dermis;
   collecting a volume of a fluid leaked from the at least one blood vessel; and
   assaying the collected fluid for the presence of one or more target analytes.

9. The method of claim 8, wherein, prior to contacting the device with the skin of a subject, at least a portion of the distal end is coated with one or more capture reagents for capturing one or more target analytes present in the leaked fluid.

* * * * *

UNITED STATES PATENT AND TRADEMARK OFFICE
CERTIFICATE OF CORRECTION

PATENT NO. : 10,500,412 B2
APPLICATION NO. : 15/545039
DATED : December 10, 2019
INVENTOR(S) : Mei X. Wu It is certified that error appears in the above-identified patent and that said Letters Patent is hereby corrected as shown below:

In the Specification

Column 1, Line 11, please insert the following paragraph:
--GOVERNMENT FUNDING
This invention was made with government support under AI089779 awarded by the National Institutes of Health. The government has certain rights in the invention.--

Signed and Sealed this
Second Day of May, 2023

Katherine Kelly Vidal
*Director of the United States Patent and Trademark Office*